United States Patent
Kahook et al.

(10) Patent No.: US 10,463,534 B2
(45) Date of Patent: Nov. 5, 2019

(54) DEVICES AND METHODS FOR CREATING A PREDICTABLE CAPSULORHEXIS OF SPECIFIC DIAMETER

(71) Applicant: THE REGENTS OF THE UNIVERSITY OF COLORADO, A BODY CORPORATE, Denver, CO (US)

(72) Inventors: Malik Y. Kahook, Denver, CO (US); Matthew Armstrong Powers, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 676 days.

(21) Appl. No.: 14/894,299

(22) PCT Filed: May 20, 2014

(86) PCT No.: PCT/US2014/038816
§ 371 (c)(1),
(2) Date: Nov. 25, 2015

(87) PCT Pub. No.: WO2014/193702
PCT Pub. Date: Dec. 4, 2014

(65) Prior Publication Data
US 2016/0166432 A1    Jun. 16, 2016

Related U.S. Application Data

(60) Provisional application No. 61/829,727, filed on May 31, 2013.

(51) Int. Cl.
*A61F 9/007* (2006.01)

(52) U.S. Cl.
CPC .......... *A61F 9/00754* (2013.01); *A61F 9/007* (2013.01)

(58) Field of Classification Search
CPC .. A61F 9/00727; A61F 9/00736; A61F 9/007; A61F 9/0133; A61F 9/0136;
(Continued)

(56) References Cited

U.S. PATENT DOCUMENTS 4,706,669 A    11/1987  Schlegel
4,766,897 A *   8/1988  Smirmaul ........... A61F 9/00754
                                                   30/263
(Continued)

FOREIGN PATENT DOCUMENTS

DE    4012882 A1   10/1991
EP    1099432 A2    5/2001
(Continued)

OTHER PUBLICATIONS

Powers, Matthew A., BA, and Malik Y. Kahook, MD. "New device for creating a continuous curvilinear capsulorhexis." *J Cataract Refract Surg 2014.* vol. 40, Issue 5, (2014) pp. 822-830 2014 © *ASCRS and ESCRS*.
(Continued)

*Primary Examiner* — Darwin P Erezo
*Assistant Examiner* — Erich Herbermann

(57) ABSTRACT

The present invention relates generally to the field of cataract surgery and more particularly to methods and apparatus for performing a capsulorhexis. This invention is in the field of medical devices. The present invention relates to a device constructed from metals, polymers or other materials that are amenable to precise surface modifications and methods for its use, wherein (1) the device assists in capsulorhexis and (2) a patterned surface having milli-, micron-, and/or nano-
(Continued)

sized micropatterning characteristics that imparts surface stabilizing and self-adhesive properties.

20 Claims, 18 Drawing Sheets

(58) Field of Classification Search
CPC ...... A61F 9/013; A61F 9/0077; A61F 9/0061; A61F 9/00754; A61F 9/00745; A61F 9/00763; A61F 2/14; A61F 2/142; A61B 17/0231; A61B 3/00; G02C 7/048
USPC .......................................... 294/1.2; 600/236
See application file for complete search history.

(56) References Cited

U.S. PATENT DOCUMENTS

| | | | |
|---|---|---|---|
| 5,135,530 A | 8/1992 | Lehmer | 606/107 |
| 5,269,787 A | 12/1993 | Cozean, Jr. et al. | 606/107 |
| 5,569,280 A | 10/1996 | Kamerling | 606/166 |
| 5,728,117 A | 3/1998 | Lash | 606/166 |
| 5,800,533 A | 9/1998 | Eggleston et al. | |
| 5,860,994 A | 1/1999 | Yaacobi | 606/166 |
| 5,873,883 A | 2/1999 | Cozean et al. | 606/166 |
| 6,436,113 B1 | 8/2002 | Burba | 606/166 |
| 6,551,326 B1 | 4/2003 | Van Heugten et al. | 606/166 |
| 8,663,235 B2 | 3/2014 | Tassignon | 606/107 |
| 9,629,747 B2 | 4/2017 | Clauson et al. | |
| 9,775,743 B2 | 10/2017 | Clauson et al. | |
| 2002/0198511 A1* | 12/2002 | Varner | A61F 9/0017 604/521 |
| 2004/0106929 A1 | 6/2004 | Masket | 606/107 |
| 2006/0100617 A1* | 5/2006 | Boukhny | A61F 9/00754 606/41 |
| 2006/0259053 A1 | 11/2006 | El-Mansoury | 606/166 |
| 2007/0049957 A1 | 3/2007 | Benitez et al. | 606/166 |
| 2007/0208422 A1* | 9/2007 | Walter | A61F 2/142 623/5.11 |
| 2008/0103367 A1* | 5/2008 | Burba | A61F 9/007 600/236 |
| 2008/0275461 A1 | 11/2008 | Nallakrishnan | 623/5.11 |
| 2009/0048619 A1 | 2/2009 | Sobel | 606/166 |
| 2010/0094415 A1 | 4/2010 | Bumbalough | |
| 2010/0145447 A1* | 6/2010 | Jia | A61B 18/14 623/6.39 |
| 2010/0179544 A1 | 7/2010 | Boukhny et al. | 606/45 |
| 2010/0274272 A1 | 10/2010 | Medina | 606/166 |
| 2011/0118734 A1 | 5/2011 | Auld et al. | 606/45 |
| 2012/0059386 A1 | 3/2012 | Sussman | 606/166 |
| 2012/0158130 A1 | 6/2012 | Moradian et al. | |
| 2012/0329905 A1* | 12/2012 | Nunez | C07C 333/04 523/113 |
| 2013/0066351 A1 | 3/2013 | Giardina et al. | 606/180 |
| 2015/0245946 A1 | 9/2015 | Fox et al. | |
| 2017/0042734 A1 | 2/2017 | Gerten | |
| 2017/0312125 A1 | 11/2017 | Clauson et al. | |
| 2018/0036171 A1 | 2/2018 | Clauson et al. | |

FOREIGN PATENT DOCUMENTS

| | | | | |
|---|---|---|---|---|
| WO | WO/2009/153550 | | 12/2009 | |
| WO | WO 2011155922 A1 * | | 12/2011 | A61B 18/08 |
| WO | WO/2013/070423 | | 5/2013 | |
| WO | WO/2014/062024 | | 4/2014 | |

OTHER PUBLICATIONS (2013) "Nottingham Cataract Device.".
Aasuri, M. K. et al. (2001) "Risk factors for and management of dropped nucleus during phacoemulsification," *Journal of Cataract & Refractive Surgery* 27(9), 1428-1432.
American Academy of Ophthalmology. (2012) "Eye-Surgery Organizations Provide Medicare-Billing Guidance to Physicians for Laser Technology Used in Cataract Procedures" *American Academy of Ophthalmology News Release.*
Apple, D. J. et al. (2000) "Surgical prevention of posterior capsule opacification: Part 1: progress in eliminating this complication of cataract surgery," *Journal of Cataract & Refractive Surgery* 26(2), 180-187.
Assia, E. I. et al. (1991) "The elastic properties of the lens capsule in capsulorhexis," *American Journal of Ophthalmology* 111(5), 628-632.
Baltussen, R. et al. (2004) "Cost-effectiveness analysis of cataract surgery: a global and regional analysis," *Bulletin of the World Health Organization* 82(5), 338-345.
Bethke, W. (2011) "Can you afford to do a femtosecond cataract?," *Review of Ophthalmology* 18, 52.
Carifi, G. et al. (2012) "Capsulorrhexis rescue techniques," *Journal of Cataract & Refractive Surgery* 38(10), 1874-1875.
Cekiç, O. et al. (1999) "The relationship between capsulorhexis size and anterior chamber depth relation," *Ophthalmic Surgery and Lasers* 30(3), 185-190.
Cimberle, M. (2012) "Femtosecond laser assisted surgery could revolutionize cataract removal in Europe," *Ocular Surgery News* 23, 1.
Coelho, R. P. et al. (2009) "Comparison of preoperative Nd:YAG laser anterior capsulotomy versus two-stage curvilinear capsulorhexis in phacoemulsification of white intumescent cataracts," *Ophthalmic Surgery, Lasers & Imaging* 40(6), 582-585.
Coelho, R. P. et al. (2012) "Capsulorhexis rescue after peripheral radial tear-out: Quick-pull technique," *Journal of Cataract & Refractive Surgery* 38(5), 737-738.
Cunningham, E. T. (2001) "World blindness—no end in sight," *British Journal of Ophthalmology* 85(3), 253-254.
Das, P. et al. (2009) "Results of intraocular lens implantation with capsular tension ring in subluxated crystalline or cataractous lenses in children," *Indian Journal of Ophthalmology* 57(6), 431-436.
Dooley, I. J. et al. (2006) "Subjective difficulty of each stage of phacoemulsification cataract surgery performed by basic surgical trainees," *Journal of Cataract & Refractive Surgery* 32(4), 604-608.
Friedman, N. J. et al. (2011) "Femtosecond laser capsulotomy," *Journal of Cataract & Refractive Surgery* 37(7), 1189-1198.
Fugo, R. J. (2006) "Fugo blade to enlarge phimotic capsulorhexis," *Journal of Cataract & Refractive Surgery* 32(11), 1900.
Gassmann, F. et al. (1988) "Anterior capsulotomy by means of bipolar radio-frequency endodiathermy," *Journal of Cataract & Refractive Surgery* 14(6), 673-676.
Hollick, E. J. et al. (1999) "The effect of capsulorhexis size on posterior capsular opacification: one-year results of a randomized prospective trial," *American Journal of Ophthalmology* 128(3), 271-279.
Izak, A. M. et al. (2004) "Analysis of the capsule edge after Fugo plasma blade capsulotomy, continuous curvilinear capsulorhexis, and can-opener capsulotomy," *Journal of Cataract & Refractive Surgery* 30(12), 2606-2611.
Karim, S. M. R. et al. (2011) "A novel technique of rescuing capsulorhexis radial tear-out using a cystotome," *Journal of Visualized Experiments*(47), 2317.
Krag, S. et al. (1993) "Strength of the lens capsule during hydroexpression of the nucleus," *Journal of Cataract & Refractive Surgery* 19(2), 205-208.
Lawani, R. et al. (2007) "[Magnitude and strategies of cataract management in the world]," *Medecine Tropicale* 67(6), 644-650.
Little, B. C. et al. (2006) "Little capsulorhexis tear-out rescue," *Journal of Cataract & Refractive Surgery* 32(9), 1420-1422.
Mohammadpour, M. (2010) "Rescue of an extending capsulorrhexis by creating a midway tangential anterior capsular flap: a novel technique in 22 eyes," *Canadian Journal of Ophthalmology / Journal Canadien d'Ophtalmologie* 45(3), 256-258.
Morgan, J. E. et al. (1996) "The mechanical properties of the human lens capsule following capsulorhexis or radiofrequency diathermy capsulotomy," *Archives of Ophthalmology* 114(9), 1110-1115.
Nagy, Z. et al. (2009) "Initial clinical evaluation of an intraocular femtosecond laser in cataract surgery," *Journal of Refractive Surgery* 25(12), 1053-1060.

(56) References Cited

OTHER PUBLICATIONS

Nagy, Z. Z. (2012) "Advanced Technology IOLs in Cataract Surgery: Pearls for Successful Femtosecond Cataract Surgery," *International Ophthalmology Clinics* 52(2), 103-114.
O'Heineachain, R. (2004) "Bag-in-the-lens IOL showing promise in prevention of PCO in paediatric eyes," *European Society of Cataract & Refractive Surgeons*.
O'Heineachain, R. (2015) New injectable lenses show promise in the restoration of accommodation, in *European Society of Cataract and Refractive Surgeons*, European Society of Cataract and Refractive Surgeons.
Ono, K. et al. (2010) "Global inequality in eye health: country-level analysis from the Global Burden of Disease Study," *American Journal of Public Health* 100(9), 1784-1788.
Palanker, D. et al. (2010) "Anterior capsulotomy with a pulsed-electron avalanche knife," *Journal of Cataract & Refractive Surgery* 36(1), 127-132.
Park, C. Y. et al. (2012) "Measurement of angle kappa and centration in refractive surgery," *Current Opinion in Ophthalmology* 23(4), 269-275.
Ram, J. et al. (1999) "Update on fixation of rigid and foldable posterior chamber intraocular lenses. part I: elimination of fixation-induced decentration to achieve precise optical correction and visual rehabilitation," *Ophthalmology* 106(5), 883-890.
Roberts, T. V. et al. (2011) "Capsular block syndrome associated with femtosecond laser—assisted cataract surgery," *Journal of Cataract & Refractive Surgery* 37(11), 2068-2070.
Sanders, D. R. et al. (2006) "Hyperopic shift in refraction associated with implantation of the single-piece Collamer intraocular lens," *Journal of Cataract & Refractive Surgery* 32(12), 2110-2112.
Singh, D. (2002) "Use of the Fugo blade in complicated cases," *Journal of Cataract & Refractive Surgery* 28(4), 573-574.
Soda, M. et al. (2012) "Effect of Decentration on the Optical Performance in Multifocal Intraocular Lenses," *Ophthalmologica* 227(4), 197-204.
Tassignon, M.-J. (2003) Bag in lens intraocular lens, in *American Society of Cataract and Refractive Surgery (ASCRS) Conference*, p. 34, Washington D.C.
Tassignon, M.-J. et al. (2006) "Ring-shaped caliper for better anterior capsulorhexis sizing and centration," *Journal of Cataract & Refractive Surgery* 32(8), 1253-1255.
Trikha, S. et al. (2013) "The journey to femtosecond laser-assisted cataract surgery: new beginnings or a false dawn?," *Eye* 27(4), 461-473.
Vaikoussis, E. et al. (1993) "Corneal endothelial damage after Nd:YAG laser anterior capsulotomy," *Documenta Ophthalmologica* 83(4), 279-286.
Wasserman, D. et al. (1991) "Anterior capsular tears and loop fixation of posterior chamber intraocular lenses," *Ophthalmology* 98(4), 425-431.
Wu, M. C. et al. (2008) "Managing the broken capsule," *Current Opinion in Ophthalmology* 19(1), 36-40.
PCT International Search Report of International Application No. PCT/US2014/038816 dated Oct. 16, 2014.

* cited by examiner

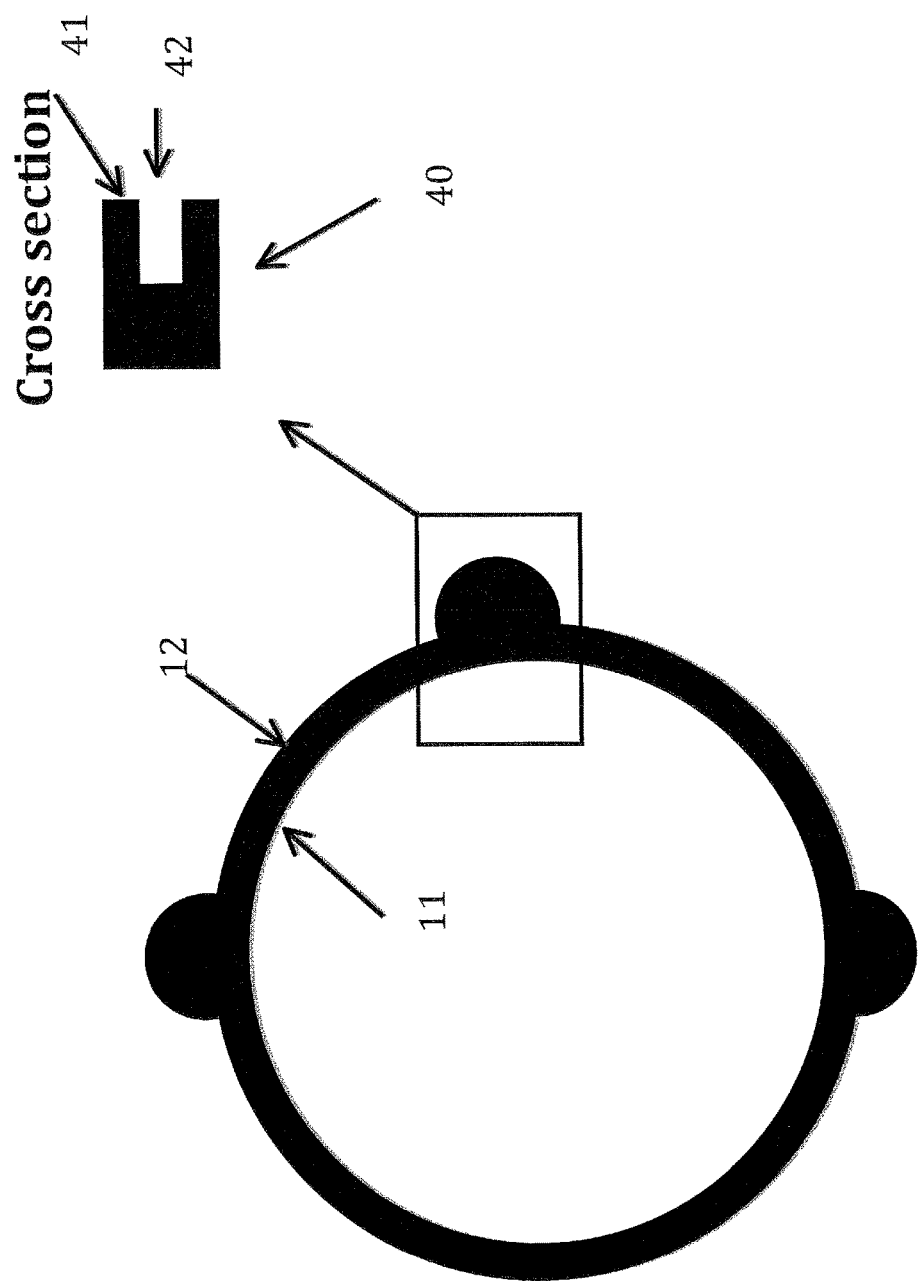

DEVICES AND METHODS FOR CREATING A PREDICTABLE CAPSULORHEXIS OF SPECIFIC DIAMETER

CROSS-REFERENCE TO RELATED APPLICATIONS

The present application claims the benefit of U.S. Provisional Patent Application No. 61/829,727, filed on. May 31, 2013, which is incorporated herein by reference.

FIELD OF THE INVENTION

The present invention relates generally to the field of cataract surgery and more particularly to methods and apparatus for performing a capsulorhexis. This invention is in the field of medical devices. The present invention relates to a device constructed from metals, polymers or other materials that are amenable to precise surface modifications and methods for its use, wherein (1) the device assists in capsulorhexis and (2) a patterned surface having micron-, and/or nano-sized patterning characteristics imparts surface stabilizing and self-adhesive properties.

BACKGROUND OF THE INVENTION

An accepted intervention for the treatment of cataracts is surgical removal of the lens and replacement of the lens function by an artificial intraocular lens (IOL). In the United States, the majority of cataractous lenses are removed by a surgical technique called phacoemulsification wherein the lens is divided into pieces and removed. Prior to removing the cataractous lens, an opening, or rhexis, must be made in the anterior capsule, a thin membrane that surrounds the lens. Currently, this opening is created by manually tearing the membrane with a surgical instrument. During phacoemulsification, there is a great deal of tension on the cut edges of the anterior capsulorhexis while the lens nucleus is emulsified. Accordingly, a continuous cut or tear ('rhexis), without "tags," is a critical step in a safe and effective phacoemulsification procedure.

If the capsule is opened with numerous small capsular tears, the small tags that remain can lead to radial capsular tears, which may extend into the posterior capsule. Such a radial tear constitutes a complication since it destabilizes the lens for further cataract removal and safe intraocular lens placement within the lens capsule later in the operation. Further, if the posterior capsule is punctured, then the vitreous may gain access to the anterior chamber of the eye. If this happens, the vitreous must be removed by an additional procedure with special instruments. The loss of vitreous is also associated with an increased rate of subsequent retinal detachment and/or infection within the eye. Importantly, these complications are potentially blinding.

Conventional equipment used for phacoemulsification includes an ultrasonically driven handpiece with an attached oscillating tip. In some of these handpieces, the operative part is a centrally located, hollow resonating bar or horn directly attached to a set of piezoelectric crystals. The crystals supply ultrasonic vibration for driving both the horn and the attached cutting tip during phacoemulsification. Prior art devices and methods used for the capsulorhexis procedure require a great deal of skill on the part of the surgeon to produce a continuous curvilinear capsular opening. This is due to the extreme difficulty in controlling the path of the cutting tip of the device. For example, a typical procedure begins with a capsular incision made with a cystotome, i.e., a cutting tip as described above. This incision is then coaxed into a circular or oval shape by pushing the leading edge of the incision in the capsule, using the cystotome as a wedge rather than as a cutting device. Alternatively, the initial capsular incision may be torn into a circular shape by grasping the leading edge with fine caliber forceps and advancing the cut. Either of these approaches involves a very challenging maneuver and the tearing motion can sometimes lead to an undesirable tear of the capsule toward the back of the lens (i.e. toward the posterior capsule), even in the most experienced hands.

Moreover, even if a smooth capsular opening without tags is ultimately produced, the size and/or position of the capsular opening may present a problem. For instance, a capsular opening that is too small can impede the safe removal of the lens nucleus and cortex and prevent proper intraocular lens insertion into the lens capsule. The additional stresses necessary to accomplish the operation with a small or misplaced capsular opening put the eye at risk for zonular and capsular breakage. Either of these complications will likely increase the length and complexity of the operation and may result in vitreous loss.

A continuous, properly positioned, and circular opening is thus highly desirable because it results in: (1) a significant reduction in radial tears and tags within the anterior capsule, (2) capsule integrity necessary for proper centering of a lens implant; and (3) safe and effective hydrodissection. In addition, the capsulorhexis should be properly dimensioned relative to the diameter of the IOL being implanted in order to reduce the chances of a secondary cataract, also called posterior capsule opacification ("PCO") and for use with proposed novel accommodative IOL designs that require close contact with the capsule. Therefore, there is a continuing need for an improved device for performing a continuous curvilinear capsulorhexis.

SUMMARY OF THE INVENTION

The present invention relates generally to the field of cataract surgery and more particularly to methods and apparatus for performing a capsulorhexis. This invention is in the field of medical devices. The present invention relates to a device constructed from metals, polymers or other materials that are amenable to precise surface modifications and methods for its use, wherein (1) the device assists in capsulorhexis and (2) a patterned surface having milli-, micro-, and/or nano-sized patterning characteristics that, upon contacting the ocular capsule surface, imparts surface stabilizing and self-adhesive properties. Some embodiments have no moving parts, while other embodiments have features that can be moved, e.g. extended. Some embodiments have tabs that extend from the ring outward to act as a barrier for iris tissue moving towards the main ring.

In one embodiment, the invention contemplates a device comprising: i) a ring having an outer surface and an inner surface; ii) a posterior surface connecting said outer surface and said inner surface, wherein said posterior surface comprises a micropattern, wherein said posterior surface is defined by an inner and outer diameter; and iii) a distinct internal edge positioned on the interface of said posterior surface and said inner surface. In one embodiment, the internal edge is at the inner diameter of said posterior surface. In one embodiment, the internal edge is a squared edge. In one embodiment, the internal edge is a sharp edge. In one embodiment, the posterior surface is defined by said an inner diameter of at least 4.3 millimeter said an outer diameter ring is greater than 7.8 millimeters. In one embodiment, the posterior surface is defined by an inner diameter is between 6.0 millimeters-4.75 millimeters. In one embodiment, said device further comprises iv) upper and lower tabs with a space between them, said tabs extending from said outer ring surface. In one embodiment, said tabs may be used to engage surrounding tissues. In one embodiment, said inner surface has an inner diameter and said outer surface has an outer diameter. In one embodiment, said ring has a 6.5 millimeter outer diameter and 5.5 millimeter inner diameter. In one embodiment, said ring has a 6.2 millimeter outer diameter and 5.0 millimeter inner diameter. In one embodiment, said ring has an outer diameter between 6.3-6.0 millimeters and and an inner diameter between 5.3-5.0 millimeters. In one embodiment, the height of the device is less than the distance between the inner ring surface and outer ring surface. In one embodiment, said internal edge of said ring is right angled in relation to the posterior surface of said ring. In one embodiment, said internal edge of said ring is 70-110 degrees in relation to the posterior surface of said ring. In one embodiment, ring is flexible. In one embodiment, said ring is made from a polymer. In one embodiment, said polymer is selected from the group consisting of: medical grade silicone, hydrophobic acrylic, hydrophilic acrylic, and other common medical grade polymers. In one embodiment, said ring further comprises a stiffened polymer backbone with a flexible coating. In one embodiment, said ring is coupled with a rigid material. In one embodiment, said rigid material is selected from the group consisting of polypropylene and nitinol. In on embodiment, the ring holds a positive or negative charge. In one embodiment, the ring is made of combined materials of variable durometer values with the lower durometer material in contact with tissue. In one embodiment, said micropattern comprises concentric micro-ridges. In one embodiment, said micropattern comprises concentric micro-grooves. In one embodiment, said posterior surface further comprises a tacky acrylic polymer with hydrophobic properties. In one embodiment, said ring is compressible and after said compression the ring returns to the ring shape. In one embodiment, the micropatterns form radial extensions from the inner to the outer ring surfaces.

In one embodiment, the invention contemplates a method, comprising:a) providing the device described above; b) making an incision in an eye, c) inserting said device through said incision, and d) positioning said device over an ocular anterior lens capsule, wherein said positioning defines an area for execution of a capsulorhexis with said device. In one embodiment, said area of execution of capsulorhexis is defined by the inner diameter of said ring. In one embodiment, said method further comprises pulling said ocular anterior lens capsule against said inner ring diameter whereupon said capsule is cut.

In one embodiment, the invention contemplates a device comprising: i) a ring having first end, a second end, an outer surface and an inner surface, wherein said first end and said second end are adjacent; ii) an opening separating said adjacent first and second ends; iii) a posterior surface connecting said outer surface and said inner surface, wherein said posterior surface comprises a micropattern; and iv) a distinct internal edge positioned on said posterior surface of said inner surface. In one embodiment, the internal edge is at the inner diameter of said posterior surface. In one embodiment, the internal edge is a squared edge. In one embodiment, the internal edge is a sharp edge. In one embodiment, said device further comprises a handle attached to said ring. In one embodiment, the posterior surface is defined by said an inner diameter of at least 4.3 millimeter said an outer diameter ring is greater than 7.8 millimeters. In one embodiment, the posterior surface is defined by said an inner diameter is between 6.0 millimeters-4.75 millimeters. In one embodiment, said device further comprises upper and lower tabs with a space between them, said tabs extending from said outer ring surface. In one embodiment, said inner surface has an inner diameter and said outer surface has an outer diameter. In one embodiment, said ring has a 6.5 millimeter outer diameter and 5.5 millimeter inner diameter. In one embodiment, said the height of the device is less than the distance between the inner ring surface and outer ring surface. In one embodiment, said internal edge of said ring is right angled in relation to the posterior surface of said ring. In one embodiment, said internal edge of said ring is 70-110 degrees in relation to the posterior surface of said ring. In one embodiment, said ring is flexible. In one embodiment, said ring is made from a polymer. In one embodiment, said polymer is selected from the group consisting of: medical grade silicone, hydrophobic acrylic, hydrophilic acrylic, and other common medical grade polymers. In one embodiment, said ring further comprises a stiffened polymer backbone with a flexible coating. In one embodiment, said ring is coupled with a rigid material configured to fix said polymer portion in place. In one embodiment, said rigid material is selected from the group consisting of polypropylene and nitinol. In one embodiment, said micropattern comprises concentric micro-ridges. In one embodiment, said micropattern comprises concentric micro-grooves. In one embodiment, said posterior surface further comprises a tacky acrylic polymer with hydrophobic properties. In one embodiment, said ring is compressible and after said compression the ring returns to the ring shape.

In one embodiment, the invention contemplates a method, comprising: a) providing the device described above; b) making an incision in an eye, c) inserting said device through said incision, and d) positioning said device over an ocular anterior lens capsule, wherein said positioning defines an area for execution of a capsulorhexis with said device. In one embodiment, said area of execution of capsulorhexis is defined by the inner diameter of said ring. In one embodiment, said method further comprises pulling said ocular anterior lens capsule against said inner ring diameter whereupon said capsule is cut.

In one embodiment, the invention contemplates a device, comprising: i) a compressible, extendable circular guide wire; ii) a guide wire with a flat posterior surface, wherein said circular guide wire comprises a ring shape when extended, wherein said ring shape comprises an outer surface and an inner surface, wherein said posterior surface is defined by an inner and outer diameter; and iii) a distinct internal edge positioned on said posterior surface of said inner surface. In one embodiment, the internal edge is at the inner diameter of said posterior surface. In one embodiment, the internal edge is a squared edge. In one embodiment, the internal edge is a sharp edge. In one embodiment, the the posterior surface is defined by said an inner diameter of at least 4.3 millimeter said an outer diameter ring is greater than 7.8 millimeters. In one embodiment, the posterior surface is defined by said an inner diameter is between 6.0 millimeters-4.75 millimeters. In one embodiment, said ring has a 6.5 millimeter outer diameter and 5.5 millimeter inner diameter. In one embodiment, said the height of the device is less than the distance between the inner ring surface and outer ring surface. In one embodiment, said internal edge of said ring is right angled in relation to the posterior surface of said ring. In one embodiment, said sharp, internal edge of said ring is 70-110 degrees in relation to the posterior surface of said ring. In one embodiment, said circular guide wire is retractable. In one embodiment, said guide wire is made from nitinol. In one embodiment, said device further comprises a cannula from which said guide wire may be extended. In one embodiment, said ring is not a closed ring.

In one embodiment, the invention contemplates a method, comprising: a) providing the device described above; b) making an incision in an eye, c) inserting said device through said incision, and d) positioning said device by extension of the guide wire over an ocular anterior lens capsule, wherein said positioning defines an area for execution of a capsulorhexis with said device. In one embodiment, said area of execution of capsulorhexis is defined by the inner diameter of said ring. In one embodiment, said method further comprises pulling said ocular anterior capsule tissue to said inner ring diameter whereupon said capsule is cut.

In one embodiment, the invention contemplates a device, comprising: i) a ring having an outer surface and an inner surface; ii) a posterior surface connecting said outer surface and said inner surface, wherein said posterior surface is defined by an inner and outer diameter; iii) a distinct internal edge positioned on said posterior surface of said inner surface; iv) a channel on the posterior surface of said ring; and v) an extendable handle with an internal lumen attached to said ring wherein said lumen connects to the channel on the posterior surface of the ring. In one embodiment, the internal edge is at the inner diameter of said posterior surface. In one embodiment, the internal edge is a squared edge. In one embodiment, the internal edge is a sharp edge. In one embodiment, the posterior surface is defined by said an inner diameter of at least 4.3 millimeter said an outer diameter ring is greater than 7.8 millimeters. In one embodiment, the posterior surface is defined by said an inner diameter is between 6.0 millimeters-4.75 millimeters. In one embodiment, said device further comprises upper and lower tabs with a space between them, said tabs extending from said outer ring surface. In one embodiment, said inner surface has an inner diameter and said outer surface has an outer diameter. In one embodiment, said ring has a 6.5 millimeter outer diameter and 5.5 millimeter inner diameter. In one embodiment, said the height of the device is less than the distance between the inner ring surface and outer ring surface. In one embodiment, said internal edge of said ring is right angled in relation to the posterior surface of said ring. In one embodiment, said sharp, internal edge of said ring is 70-110 degrees in relation to the posterior surface of said ring. In one embodiment, said ring is made from a polymer. In one embodiment, said ring is flexible. In one embodiment, said polymer is selected from the group consisting of: medical grade silicone, hydrophobic acrylic, hydrophilic acrylic, and other common medical grade polymers. In one embodiment, said ring further comprises a stiffened polymer backbone with a flexible coating. In one embodiment, said ring is coupled with a rigid material configured to fix said polymer portion in place. In one embodiment, said rigid material is selected from the group consisting of polypropylene and nitinol. In one embodiment, said ring is compressible. In one embodiment, said ring is compressible and after said compression the ring returns to the ring shape.

In one embodiment, the invention contemplates a method, comprising: a) providing the device described above; b) making an incision in a clear cornea of an eye, c) inserting the ring portion of said device through said incision, d) positioning the ring portion of said device over an ocular anterior capsule, wherein said positioning defines an area for execution of a capsulorhexis with said device, and e) applying suction to said lumen such that said device is retained in position. In one embodiment, said area of execution of capsulorhexis is defined by the inner diameter of said ring. In one embodiment, said method further comprises pulling said ocular anterior capsule tissue to said inner ring diameter whereupon said capsule is cut.

In a first embodiment, the invention contemplates an ophthalmic device, comprising: a ring, said ring comprising i) an outer surface and an inner surface, ii) a sharp, internal edge and iii) a (substantially) flat posterior surface, wherein said inner surface defines an area configured in size to be smaller than the surface area of an ocular anterior lens capsule, and wherein said posterior surface comprises a micropattern configured for selectively retaining of said ring on said anterior lens capsule. In one embodiment, said sharp internal edge is the bottom or posterior surface inner edge of said ring. In one embodiment, said sharp, internal edge of said ring is right angled. In one embodiment, said sharp, internal edge of said ring is 70-110 degrees in relation to the posterior surface of said ring. In one embodiment, said sharp, internal edge of said ring are near 90 degree angle in relation to the posterior surface, such as sloping angle (100 degrees) or an angle of 80 degrees. In one embodiment, the angle of said sharp, internal edge is between 80 and 100 degrees in relation to the posterior surface of said ring. In one embodiment, said sharp, internal edge of said ring comprises a concavely curved inner surface with a sharp posterior edge. In one embodiment, said sharp, internal edge of said ring comprises a convexly curved inner surface with a sharp posterior edge. In one embodiment, the size of the (substantially circular) area defined by said inner surface of said ring is less than the surface area of said ocular anterior lens capsule. In one embodiment, the size of the area defined by said inner surface of said ring is between 30-70% of the surface area of said ocular anterior lens capsule. In one embodiment, the size of the area defined by said inner surface of said ring is between 30-50% of the surface area of said ocular anterior lens capsule. In one embodiment, the area defined by said inner surface of said ring is between 7.8 millimeters-4.9 millimeters. In one embodiment, the size of the area defined by said inner surface of said ring is between 6.4 millimeters to 4.3 millimeters. In one embodiment, the size of the area defined by said inner surface of said ring is between 6.0 millimeters to 4.75 millimeters. The anterior lens capsule is typically 9-11 millimeters in diameter in the adult human and 8-9 millimeters in newborn children. In one embodiment, the size of the area defined by said inner surface of said ring is a circular area with a defined diameter of between 7.8 millimeters to 4.9 millimeters for adults. In one embodiment, the size of the area defined by said inner surface of said ring is a circular area with a defined diameter of between 6.4 millimeters to 4.3 millimeters for newborn children. In one embodiment, said device further comprises upper and lower tabs with a space between them, said tabs extending from said outer ring surface to engage surrounding tissues. In one embodiment, said tissues comprise the iris. In one embodiment, said tabs may be offset superiorly to receive iris tissue without lifting the ring from a specific position such as the surface of an anterior capsule. In one embodiment, the height of the device is less than the distance between the inner ring surface and outer ring surface. In one embodiment, said sharp, internal edge of said ring is right angled in relation to the posterior surface of said ring. In one embodiment, said sharp, internal edge of said ring is 70-110 degrees in relation to the posterior surface of said ring. In one embodiment, said ring is flexible. In one embodiment, said ring is made from a polymer. In one embodiment, said polymer is selected from the group consisting of: medical grade silicone, hydrophobic acrylic, hydrophilic acrylic, and other common medical grade polymers. In one embodiment, said ring comprises medical grade silicone. In one embodiment, said ring further comprises a stiffened polymer backbone with a flexible coating. In one embodiment, ring is coupled with a rigid material configured to fix said polymer portion in place. In one embodiment, said rigid material is selected from the group consisting of polypropylene and nitinol. In one embodiment, said inner surface has an inner diameter (defined by a straight line going from the inner surface on one side of the ring to the inner surface on the other side of the ring) and said outer surface has an outer diameter (defined by a straight line going from the outer surface on one side of the ring to the outer surface on the other side of the ring). In one embodiment, said ring has an inner diameter between 4.75 millimeters to 6.0 millimeters and an outer diameter between 5.0 millimeters to 8.5 millimeters. In one embodiment, said ring has a 6.5 millimeter outer diameter and 5.5 millimeter inner diameter. In one embodiment, the inner and outer diameters can be substantially smaller, such as 1 millimeter inner diameter and 3 millimeter outer diameter and the like. In one embodiment, the inner and outer diameters are between 1 millimeter and 8 millimeters, and more preferably between 1 and 6.5 millimeters. In one embodiment, the thickness (the difference between the inner and outer diameter) of said ring may vary, for example from 1 millimeter to 0.05 millimeters. The ring is generally designed so that the height of the device is less than the width between the inner and out ring borders. In one embodiment, the height (the difference between the top (anterior) and bottom (posterior) surfaces) of said ring may vary, for example from 1 millimeter to 0.05 millimeters. In one embodiment, said ring further comprises positioning holes. In one embodiment, said positioning holes are placed to enable horizontal positioning on the capsule. In one embodiment, said positioning holes are placed to enable vertical positioning. In one embodiment, said positioning holes enable positioning and are used to facilitate moving the device from side to side or up and down on the capsule surface and used to help insert or extract the device through an incision. In one embodiment, said micropattern comprises concentric micro-ridges. In one embodiment, said micropattern comprises concentric micro-grooves. In one preferred embodiment, said micropattern is between 1 and 50 microns in width for each etched feature. In one embodiment, the micropattern upon the posterior surface of the device comprises a micropatterned geometrical pattern, said pattern having a plurality of grooves between a plurality of raised surfaces. In one embodiment, said pattern is selected from the group consisting of vertical, horizontal, circular, intersecting grid, and concentric rings. In one embodiment, said grooves are patterned in a vertical orientation. In one embodiment, said grooves are patterned in a horizontal orientation. In one embodiment, said grooves are patterned in a diagonal orientation. In one embodiment, said grooves are patterned in a helical orientation. In one embodiment, said geometrical pattern further comprises a columnar structure. In one embodiment, said geometrical pattern provides additional adherence to a tissue surface. In one embodiment, said posterior surface further comprises a tacky acrylic polymer with hydrophobic properties. In one embodiment, said ring is compressible and after said compression the ring returns to the ring shape. In one embodiment, said device can be inserted through an incision less than 2.4 millimeters wide and return to original pre-insertion form (i.e. shape) in less than 30 seconds.

In one embodiment, the invention contemplates a method, comprising: a) providing the first embodiment of the device described above; b) making an incision in a clear cornea of an eye, c) inserting said device through said incision, and d) positioning said device over an ocular anterior lens capsule, wherein said positioning defines an area for execution of a capsulorhexis with said device. In one embodiment, said area of execution of capsulorhexis is defined by the inner diameter of said ring. In one embodiment, said method further comprises pulling said ocular anterior lens capsule against said inner ring diameter whereupon said capsule is cut. In one embodiment, said positioning holes of said device enable positioning on the capsule and are used to facilitate moving the device from side to side or up and down and used to help insert or extract the device through an incision.

In a second embodiment, the invention contemplates an ophthalmic device, comprising: a compressible, extendable circular guide wire comprising a sharp, internal edge and a flat posterior surface, wherein said circular guide wire comprises a ring shape when extended and said ring shape comprises an outer surface and an inner surface wherein said inner surface defines an area (that is substantially circular, oval or elliptical) configured in size to be smaller than the surface area of an ocular anterior lens capsule. In one embodiment, said circular guide wire is compressible and retractable. In one embodiment, said guide wire is made from nitinol. In one embodiment, said device further comprises a cannula or tube (covering, surrounding or housing the guide wire) from which said guide wire may be extended (e.g. outwardly and away from said cannula, tube or housing). In one embodiment, the size of the area defined by said inner surface of said ring is less than the surface area of an ocular anterior lens capsule. In one embodiment, the size of the area defined by said inner surface of said ring is between 30-70% of the surface area of said ocular anterior lens capsule. In one embodiment, the size of the area defined by said inner surface of said ring is between 30-50% of the surface area of said ocular anterior lens capsule. In one embodiment, said inner surface has an inner diameter and said outer surface has an outer diameter (as defined previously). In one embodiment, said ring has a 5.5 millimeter inner diameter. In one embodiment, said ring has a 6.5 millimeter outer diameter and 5.5 millimeter inner diameter. In one embodiment, the inner and outer diameters can be substantially smaller, such as 1 millimeter inner diameter and 3 millimeter outer diameter and the like. In one embodiment, the inner and outer diameters are between 1 millimeter and 8 millimeters, and more preferably between 1 and 6.5 millimeters. In one embodiment, the thickness (the difference between the inner and outer diameter) of said ring may vary, for example from 1 millimeter to 0.05 millimeters. In one embodiment, said ring is not a closed ring (i.e. it may have an opening as shown in some of the figures herein).

In one embodiment, the invention contemplates a method, comprising: a) providing the second embodiment of the device described above; b) making an incision in a clear cornea of an eye, c) inserting said device through said incision, and d) positioning said device by extension of the guide wire over an ocular anterior lens capsule surface, wherein said positioning defines an area for execution of a capsulorhexis with said device. In one embodiment, said area of execution of capsulorhexis is defined by the inner diameter of said ring. In one embodiment, said method further comprises pulling said ocular anterior capsule tissue to said inner ring diameter whereupon said capsule is cut.

In yet a third embodiment, the invention contemplates an ophthalmic device, comprising: a ring, said ring comprising i) an outer surface and an inner surface, wherein said inner surface defines an area configured in size to be smaller than the surface area of an ocular anterior lens capsule, ii) an internal edge, and iii) a channel on the posterior surface of the ring, and iv) an extendable handle with an internal lumen attached to said ring wherein said lumen connects to the channel on the posterior surface of the ring. In one embodiment, the size of the area defined by said inner surface of said ring is less than the surface area of said ocular anterior lens capsule. In one embodiment, the size of the area defined by said inner surface of said ring is between 30-70% of the surface area of said ocular anterior lens capsule. In one embodiment, the size of the area defined by said inner surface of said ring is between 30-50% of the surface area of said ocular anterior lens capsule. In one embodiment, said ring is made from a polymer. In one embodiment, said ring is flexible. In one embodiment, said polymer is selected from the group consisting of medical grade silicone, hydrophobic acrylic, hydrophilic acrylic, and other common medical grade polymers. In one embodiment, said ring further comprises a stiffened polymer backbone with a flexible coating. In one embodiment, said ring is coupled with a rigid material configured to fix said polymer portion in place. In one embodiment, said rigid material is selected from the group consisting of polypropylene and nitinol. In one embodiment, said inner surface has an inner diameter and said outer surface has an outer diameter. In one embodiment, said ring has a 6.5 millimeter outer diameter and 5.5 millimeter inner diameter. In one embodiment, said ring is compressible and after said compression the ring returns to the ring shape.

In one embodiment, the invention contemplates a method, comprising: a) providing the third embodiment of the device described above; b) making an incision in a clear cornea of an eye, c) inserting the ring portion of said device through said incision, d) positioning the ring portion of said device over an ocular anterior capsule, wherein said positioning defines an area for execution of a capsulorhexis with said device, and e) applying suction to said lumen such that said device is retained in position. In one embodiment, said area of execution of capsulorhexis is defined by the inner diameter of said ring. In one embodiment, wherein said method further comprises pulling said ocular anterior capsule tissue to said inner ring diameter whereupon said capsule is cut.

It is not intended that embodiments of the invention be limited to any particular method or device confirmation; however, it is believed that the device may be optimally designed to enable capsulorhexis.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As used herein, the terms "prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the terms "medication" or "therapeutic agent" refer to something that treats or prevents or alleviates the symptoms of a disease or condition, a drug or pharmaceutical composition. Medication is considered to be delivered or present in therapeutically effective amounts or pharmaceutically effective amounts.

As used herein, the terms "medical device," "implant," "device," "medical device," "medical implant," "implant/device," and the like are used synonymously to refer to any object that is designed to be placed partially or wholly within a patient's body (whether permanently or temporarily) for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. While medical devices are normally composed of biologically compatible synthetic materials (e.g., medical-grade stainless steel, titanium and other metals; exogenous polymers, such as polyurethane, silicon, PLA, PLGA, PGA, PCL), other materials may also be used in the construction of the medical implant.

As used herein, the term "ring" refers to generally to a substantially circular shape (e.g. a circle, oval, or ellipse), but not necessarily one without small gaps or openings. A ring as described herein need not be a completely closed loop. Indeed, embodiments are shown in the figures where there is a small opening in the circle or ring.

As used herein, the terms "cannula" refers to a tube that may surround a device or other components of a device, such as an extendable handle described herein. In some embodiments, the cannula can be inserted into the body.

As used herein, the terms "superior" and "posterior" refer to the portion furthest from, and closest to, the patient, respectively.

As used herein, the term "micropatterning" preferably refers to millimeter, micrometer, and/or nanometer scale surface modifications including but not limited to laser etching, chemical etching, photo-etching, photolithography, machining, stamping, deposition processes, mechanical drilling, molding, 3D printing, Atomic Layer Deposition or other means of modifying surfaces.

As used herein, the term "implanted" refers to having completely or partially placed a device within a host. A device is partially implanted when some of the device reaches, or extends to the outside of, a host.

The present invention contemplates devices configured to be compatible with the ocular lens capsule. As used herein, the term "compatible" refers to an articulation of elements that conforms closely to anatomical features and device features or surfaces. For example, in one embodiment, the present invention contemplates a ring configured and dimensioned such that it can rest on the capsule surface and define a portion of the capsule surface for the surgery.

As used herein, the term "nitinol" refers to a metal alloy of nickel and titanium, where the two elements are present in roughly equal atomic percentages. Nitinol alloys exhibit two closely related and unique properties: shape memory and superelasticity (also called pseudoelasticity). Shape memory refers to the ability of nitinol to undergo deformation at one temperature, and then recover its original, undeformed shape upon heating above its "transformation temperature". Superelasticity occurs at a narrow temperature range just above its transformation temperature; in this case, no heating is necessary to cause the undeformed shape to recover, and the material exhibits enormous elasticity, some 10-30 times that of ordinary metal.

Any concentration range, percentage range, or ratio range recited herein are to be understood to include concentrations, percentages or ratios of any integer within that range and fractions thereof, such as one tenth and one hundredth of an integer, unless otherwise indicated. In addition, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to either one polymer or a mixture comprising two or more polymers. As used herein, the term "about" means±15%.

As used herein, the term "sinskey hook" refers to angulated round hook with a handle used in insertion of an intraocular lens and other ophthalmological procedures.

As used herein, the term "tacky acrylic polymer with hydrophobic properties" refers to a material made of common monomers to form a hydrophobic acrylic structure that has a low glass transition temperature and adheres to surfaces.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1A shows the device 1 contains a nitinol core/blade 2 which fits inside the exterior tubing 3. FIG. 1B shows a top view of the device 1 which has an extended straight portion of the device 4 and a circular portion of the device 5. FIG. 1B shows (which has a small opening 8) and the area defined by the ring 17 and the inner 14 and outer 15 diameters of the circular portion device 5. FIG. 1C shows a side view of the device 1 and the inner 11 and outer 12 surfaces of the ring. FIG. 1D shows the circular portion of the device 5 which contains the sharpened inward beveled edge 7. FIG. 1E shows another side view of the device 1 which has an extended straight portion of the device 4 and a circular portion of the device 5 connected by an angled neck of the device 6.

FIG. 3A shows the retracted device 19 with the cannula 20 approximately 1.5 to 2 millimeters wide. FIG. 3B shows the device 19 with the guide wire extended 21. FIG. 3C shows a side view of the extended guide wire 21. The circular portion of the guide wire 23 is approximately 5 to 5.5 millimeters wide and extends 2 millimeters out from the cannula 20. FIG. 3C diagrammatically shows where the diameter of the ring 14 is less than the diameter of the capsule membrane 16. FIG. 3D shows a side view of the nitinol guide wire device 19 showing the extendable guide wire 21 and the circular portion of the guide wire 23. FIG. 3D also shows the inner 11 and outer 12 surfaces of the ring, which has a small opening 8. FIG. 3E shows a cross-section of the guide wire 21, which is approximately 0.35 millimeters wide.

FIG. 12 shows the diameter defined by the outer diameter 15 (0.68) and inner diameter 14 (0.55).

FIG. 19 shows one embodiment of the device wherein the ring may contain upper 41 and lower 40 tabs with a gap in between 42 that extend from the outer surface of the ring for some distance and contain any encroaching tissues, such as iris, away from the ring surface. The upper and lower tabs can be found spaced at variable distances around the outer ring surface. The tabs may be offset slightly to receive iris tissue without displacing the bottom or posterior surface 13 of the device from a given plane.

Figure 1:
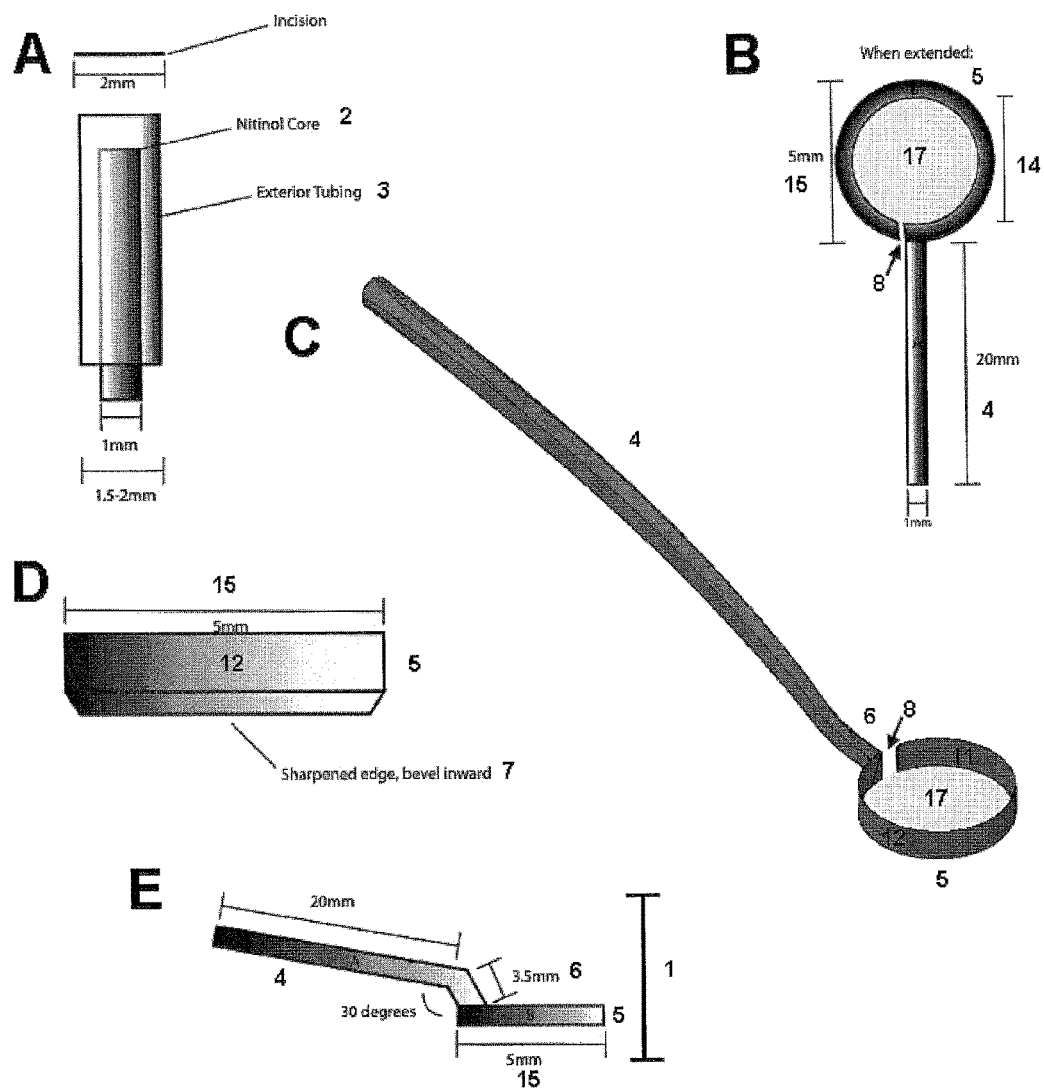
FIG. 1 shows the first embodiment of the device, a nitinol knife.

LIST OF REFERENCE NUMERALS 1 the first embodiment device
2 the nitinol core/blade
3 the exterior tubing
4 the extended straight portion of the device
5 the circular portion of the device
6 the angled neck of the device
7 the sharpened inward beveled edge
8 small opening in the ring
9 anterior capsule/membrane
10 path of capsulorhexis tissue removal
11 the inner surface of the ring
12 the outer surfaces of the ring
13 the posterior surface of the ring
14 the inner ring diameter
15 the outer ring diameter
16 diameter of the capsule membrane
17 area defined by the ring (whether measured from inner surface to inner surface or measured from outer surface to outer surface)
18 the total surface area of the capsule
19 the second embodiment device
20 cannula
21 nitinol guide wire
22 the angled neck of the device
23 deployed circular guide wire
24 the third embodiment of the device
25 the posterior suction ring
26 the channeled section on the posterior surface 13 of the ring portion of the device.
27 the handle portion of the device
28 the lumen of the handle which connects with the posterior suction ring
29 the fourth embodiment of the device
30 the nitinol wire
31 silicone ring that articulates with the nitinol wire
32 incision
33 forceps
34 excised tissue
35 the fifth embodiment of the device
36 horizontal positioning holes/cavitation through the fifth embodiment, used for manipulation with a sinskey hook or other similar device
37 a top side circular depression in the fifth embodiment of the device and is used to allow for a device to sit in the depression to push the device against the capsule if needed
38 vertical positioning holes/spherical indentation for application of downward pressure
39 micropatterning
40 lower tab extending from outer diameter of the ring 15
41 upper tab extending from outer diameter of the ring 15

42 gap between upper tab 41 and lower tab 40 to hold iris or other tissues away from the ring micropatterning

DESCRIPTION OF THE INVENTION

The present invention relates generally to the field of cataract surgery and more particularly to methods and apparatus for performing a capsulorhexis. This invention is in the field of medical devices. The present invention relates to a device constructed from metals, polymers or other materials that are amenable to precise surface modifications and methods for its use, wherein (1) the device assists in capsulorhexis and (2) a pattered surface having micron-, and/or nano-sized micropatterning characteristics that imparts surface stabilizing properties.

In one embodiment, the present invention contemplates a device and method for creating a continuous curvilinear capsulorhexis (CCC-opening) in the anterior and/or posterior capsule of the mammalian ocular lens. In one embodiment, the device is inserted into the eye through a micro-incision (≤2.4 millimeters) made in a clear cornea. The device is then inserted into the eye and placed over the anterior capsule. A CCC is then made using the device as a guide to achieve an exact diameter for the opening. The device acts as a barrier to the rhexis running to the periphery of the capsule that, if it were to occur, causes harm to the patient and a "dropped nucleus". The device is made of a flexible polymer (medical grade silicone, hydrophobic or hydrophilic acrylic or other common polymer of medical grade quality) and may be coupled with polypropylene, nitinol or other more rigid materials to fix the polymer portion in place over the capsule. The bottom part or posterior surface of the polymer may be micropatterned or roughened to increase adhesion and decrease slippage over the capsule in an aqueous environment. In addition, use of a tacky acrylic polymer with hydrophobic properties on the contact surface, used under viscoelastic may increase adhesion to the capsule, potentially obviating the simultaneous need for the nitinol ring. Suction can be applied in some versions through ports present within the polymer ring (or handle), although it was indicated that the suction aspect is optional and only one possible embodiment. The device might be inserted through a 1-millimeter paracentesis. The device might be coupled with an inserter that allows for folding within the inserter and injection into the eye anterior chamber and over the lens capsule in a minimally traumatic fashion.

Herein, the evolution of a novel device for facilitation of a manual continuous curvilinear capsulorhexis (CCC) is described, with a specific focus on efficacy, ease of adoption across a wide range of user experience, access through a small incision and cost of goods.

Benchside ex vivo testing of several unique prototypes for guidance and assistance of CCC in bovine and human eyes was performed. Five broad designs were tested: a flexible circular knife constructed of nickel-titanium alloy (nitinol), a flexible guide wire constructed of nitinol, a flexible suction device constructed of elastomeric material, a combination approach of a nitinol guide wire and flexible silicone ring and a free standing micropatterned silicone ring.

The first three designs were not readily amenable to insertion through a sub-2.4 millimeters clear corneal incision and provided less than optimum downward force to cut the capsule and/or prevent radial tears. The fourth design was successfully inserted through a 2.4 millimeters corneal incision, and maintained adequate downward pressure and contact with the capsule to guide a manual CCC without radial tears. The final design was insertable through a 2.4 millimeter incision and exhibited self-adhesive characteristics after placement on the anterior capsule with viscoelastic filling the anterior chamber.

Given the steep learning curve for performing manual capsulorhexis and an extremely high cost for newly introduced CCC assistive devices such as femtosecond laser, an alternative approach for creating a CCC is desirable. Performance of a highly precise manual CCC through a small incision using inexpensive materials is a viable alternative for resource-limited settings and across a wide range of user experience.

Herein, the development of a novel device made of commonly used inexpensive medical materials that would allow surgeons to perform CCC through a small incision (≤2.4 millimeters) is described. The focus of development was the achievement of precise and predictable CCC diameters using standard techniques and on the ease of adoption across a wide range of user experience.

Methods

Benchside testing of several novel devices and techniques were performed in both bovine and human ex vivo environments. In testing of each device embodiment, eyes were mounted in a Styrofoam holder and held in place using four pins. Corneal incisions were made using a 2.4 millimeters keratome blade. Cohesive viscoelastic was injected into the anterior chamber followed by insertion of the devices through the corneal incision. Under microscopic visualization, CCC was initiated with a Utrata capsulorhexis forceps within the interior hole of each device. Ease of inserting the device through the corneal incision and successful performance of a circular continuous capsulorhexis of 5.5 millimeters diameter, measured by calipers, was assessed.

Results

Embodiment 1: Nitinol Knife

Initially, a flexible circular nitinol blade was designed that could be inserted into the anterior chamber through a cannula. Nitinol is a 1:1 nickel:titanium alloy most common used for expandable stents. The alloy has both shape memory and superelastic properties. The design took advantage of the alloy's superelasticity. The device was designed so that the blade would be retracted into a cannula, which would then be inserted into a corneal incision. The nitinol blade would then be deployed inside the anterior chamber, where it would reassume its circular shape. The blade would then be used to cut the capsule in "cookie cutter" fashion. A contract manufacturer supplied the nitinol prototypes based on computer-aided design (CAD) files provided, and the bottom edge was sharpened with a drummel. See FIG. 1 for original design.

Figure 2:
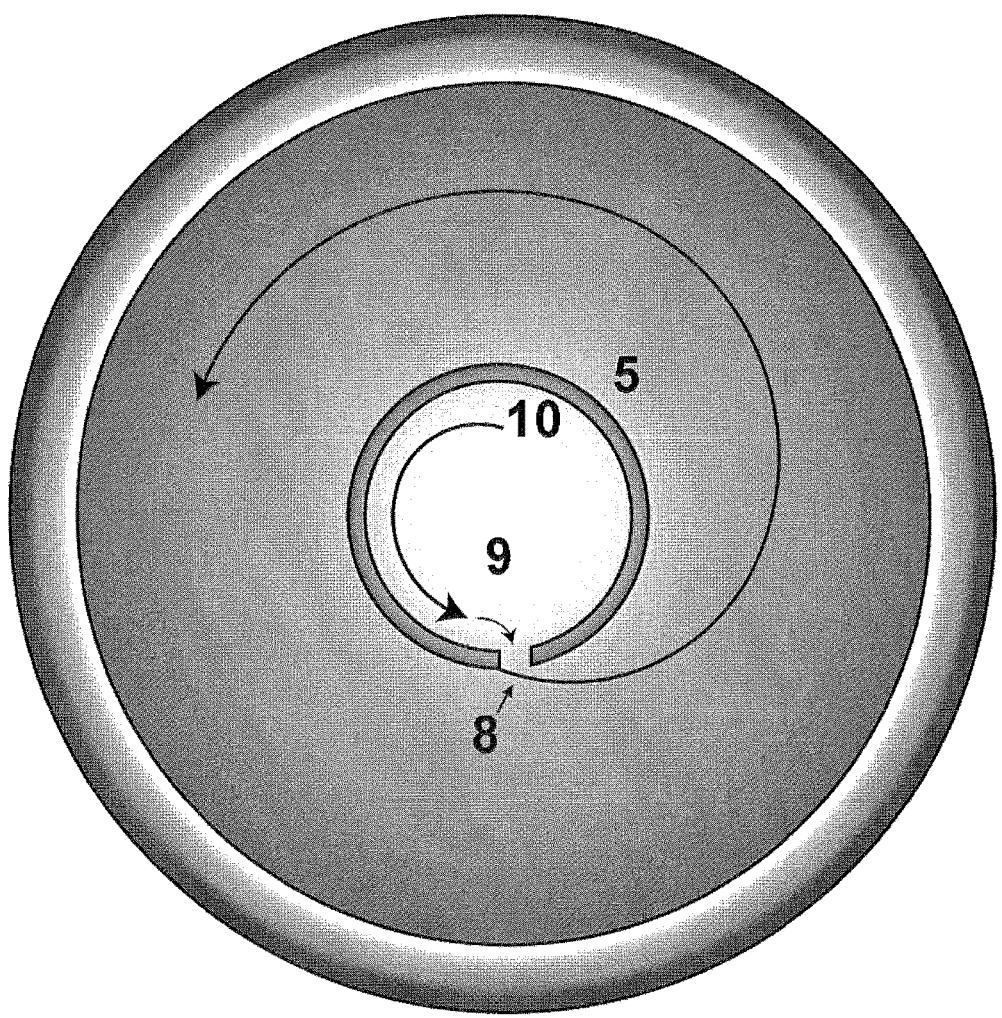
FIG. 2 shows the results of nitinol knife 1 experiments. Herein the circular portion of the device 5 is positioned on the anterior capsule of the eye 9 after the device 1 is extended into an incision. Forceps or some other means are used to remove the portion of the anterior capsule of the eye 9 by shear and stretch forces. This results in a path of capsulorhexis tissue removal 10. In this embodiment, the small opening 8 in the ring portion of the device resulted in the path of capsulorhexis tissue removal 10 extending beyond the area defined by the inner circular portion of the device 5.

The nitinol blade was tested in a bovine ex vivo environment. Because of difficulty with minimally invasive insertion of the blade into the anterior chamber through a 2.4 millimeters incision, corneas were removed with corneal scissors and an open-sky approach was used. Viscoeslastic was injected above the capsule and the nitinol blade was pressed on to the capsule using a hemostat. In all bovine samples, this resulted in radial tears, usually through the discontinuous section of the blade (FIG. 2). It was decided not to proceed with human eye testing and to reassess the approach.

Embodiment 2: Nitinol Guide Wire

Figure 3:
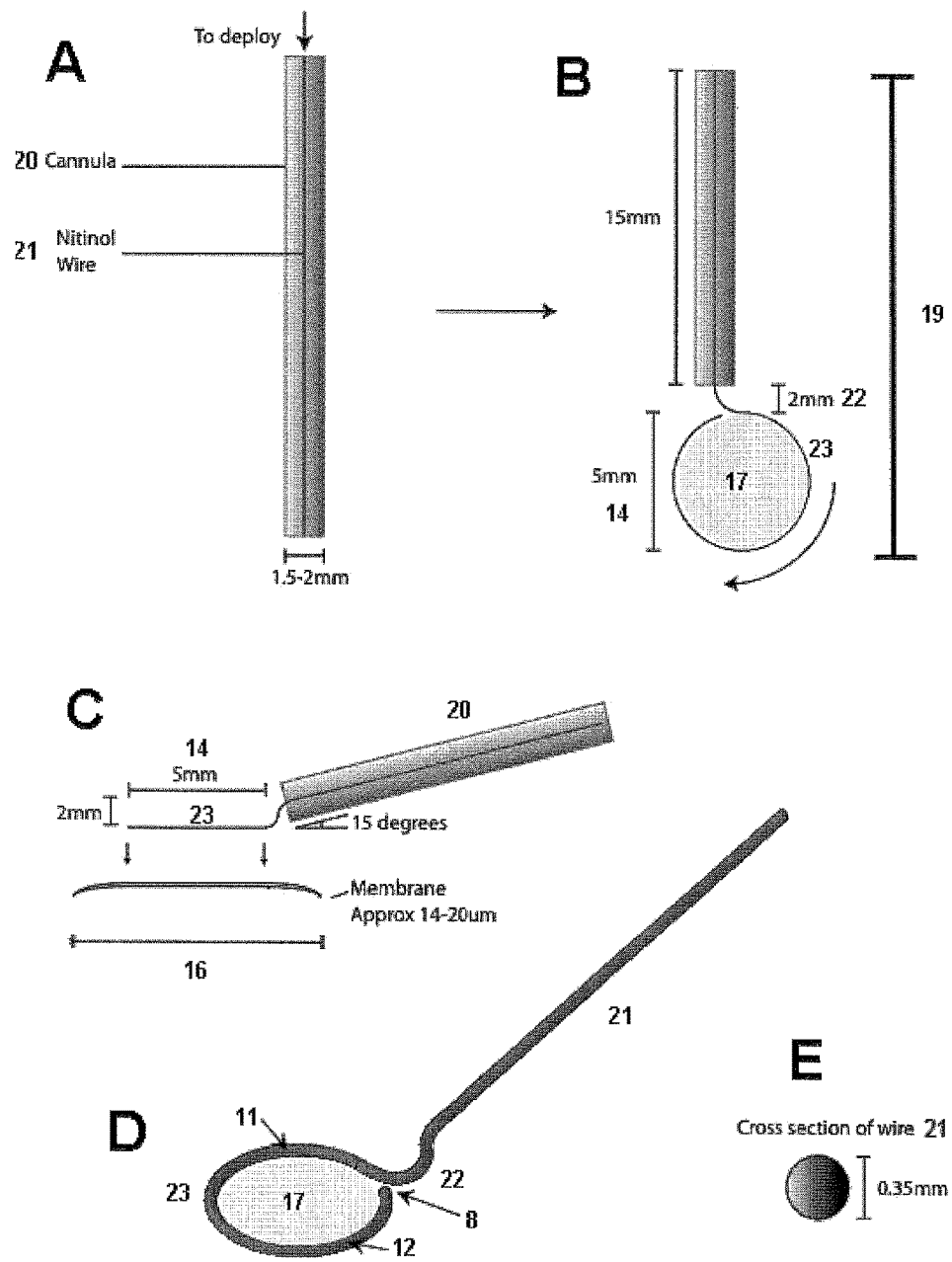
FIG. 3 shows the initial design of a nitinol guide wire device 19, the second embodiment device. The guide wire 21 is retracted into a cannula 20, but when the guide wire is deployed 23 it forms a circular portion.
Figure 4:
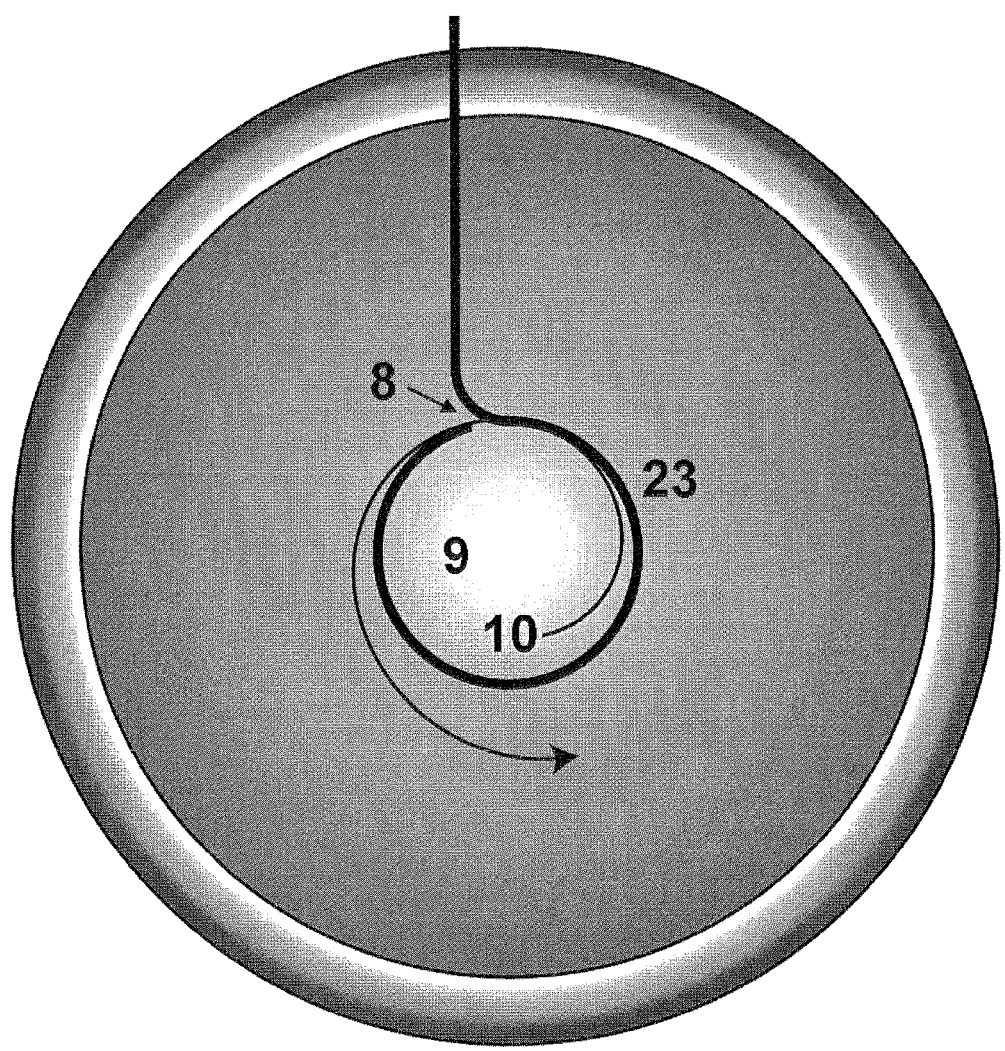
FIG. 4 shows the results of nitinol guide wire 19 experiments of the second embodiment device 19. Herein the circular portion of the guide wire 23 is positioned on the anterior capsule of the eye 9 after the device 19 is extended into an incision. Forceps or some other means are used to remove the portion of the anterior capsule of the eye 9 by shear and stretch forces. This results in a path of capsulorhexis tissue removal 10. In this embodiment, the small opening 8 in the ring portion of the device resulted in the path of capsulorhexis tissue removal 10 extending beyond the area defined by the inner circular portion of the guide wire 23.

The results of the first embodiment caused a reconsideration of the strategy of a cutting device. The strategy was changed to guiding a manual capsulorhexis inside a circular device 19. A guide wire 21 was designed, again made from nitinol. Deployment through the incision was similar to the first device 1; the wire 21 was drawn into a cannula 20, inserted into a corneal incision, and then deployed in the anterior chamber, see FIG. 3. The wire 21 rested on top of the capsule, allowing for guidance of a manual capsulorhexis using standard techniques with an Utrata forceps. Prototypes were made by a contract manufacturer based on CAD's provided. There was difficulty inserting the device 19 through a corneal incision due to the curving of the alloy as it entered into the anterior chamber. The prototypes were tested in a bovine ex vivo eye open-sky environment. In each experiment, the guide wire sat flush on the capsule, and guided the rhexis to some degree for one to two clock hours. However, guidance was insufficient to prevent radial tears from occurring underneath the wire when trying to re-grasp the capsule and advance the rhexis, see (FIG. 4). It was decided not to proceed with human eye testing and to reassess the approach.

Embodiment 3: Flexible Suction Ring

Figure 5:
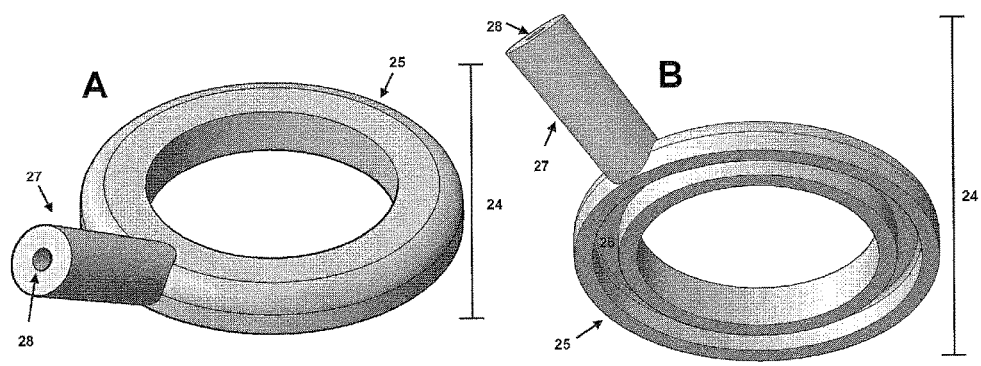
FIG. 5 shows the design of the third embodiment of the device 24, which contains a posterior suction ring, the channeled 26 on the posterior surface of the ring portion of the device 25. The device further has a handle portion of the device 27 that contains a lumen 28, which connects with the posterior suction ring. A suction means (not shown) can be connected to apply suction through the lumen.
Figure 6:
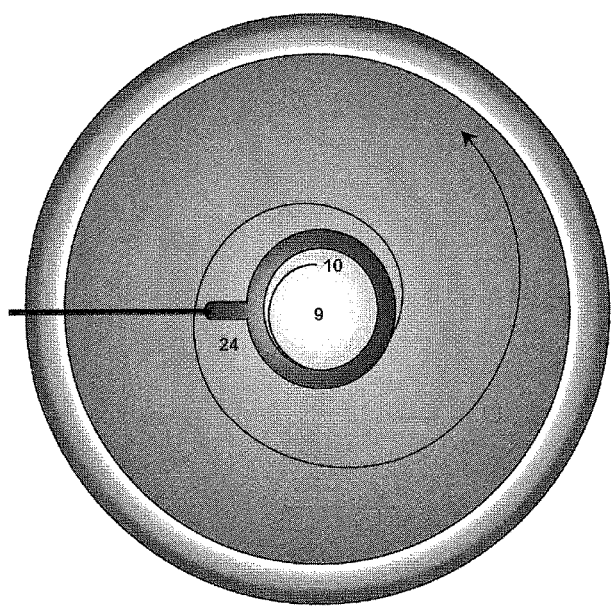
FIG. 6 shows the results of suction ring 24 testing. Herein the posterior suction ring, a channel 26 encircles the posterior surface 13 of the ring portion of the device 25 and is positioned on the anterior capsule of the eye 9 after the device 19 is extended into an incision and suction was applied to keep the device 19 in position. Forceps 33 or some other means are used to remove the portion of the anterior capsule of the eye 9 by shear and stretch forces. This results in a path of capsulorhexis tissue removal 10. In this embodiment, the path of capsulorhexis tissue removal 10 extending beyond the area defined by the inner circular portion of posterior suction ring, the channel 26 on the posterior surface 13 of the ring portion of the device 25. It is thought that perhaps the suction was not sufficient to allow the device to operate as intended.

This embodiment maintained the concept of CCC guidance, but moved away from nitinol as a material, as well as the use of manual downward pressure as a method of adherence to the capsule. It was felt that the downward pressure used in the previous embodiments was not optimum. Instead, a flexible polymeric device capable of producing suction against the capsule was designed, which theoretically would provide adequate adhesion in order to guide a CCC, see FIG. 5. The prototype was again made by a contract manufacturer based on the furnished CAD's. The device was first tested in ex vivo bovine eyes. The device was folded and insertion through a 2.4 millimeter incision was attempted but it was deemed too small for atraumatic entry, and so an open sky technique was adopted. The device was placed on top of the capsule, and suction was generated using a 27-guage needle attached to an extension of the ring prototype. Unfortunately none of the devices tested provided optimum suction to allow for guidance of the rhexis. This was in part due to occlusion of the suction ports by viscoelastic as well as difficulty in generating suction on the thin anterior capsule. Even when suction to the capsule was partially achieved, performing the rhexis tended to break the seal and send the tear radially, see FIG. 6. It was decided not to proceed with human eye testing and to reassess the suction approach.

Embodiment 4: Combination Nitinol & Silicone Ring

Figure 7:
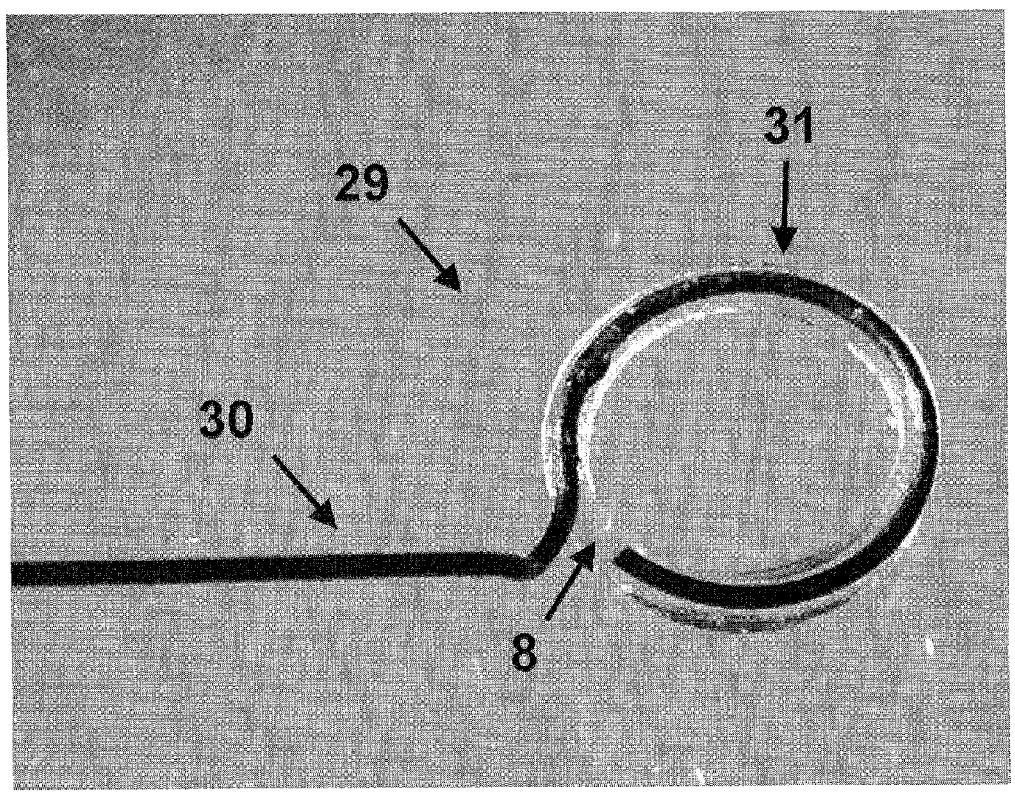
FIG. 7 shows the fourth embodiment of the device 29, which contains nitinol wire 30 and silicone ring 31. The ring has a small opening 8.
Figure 8:
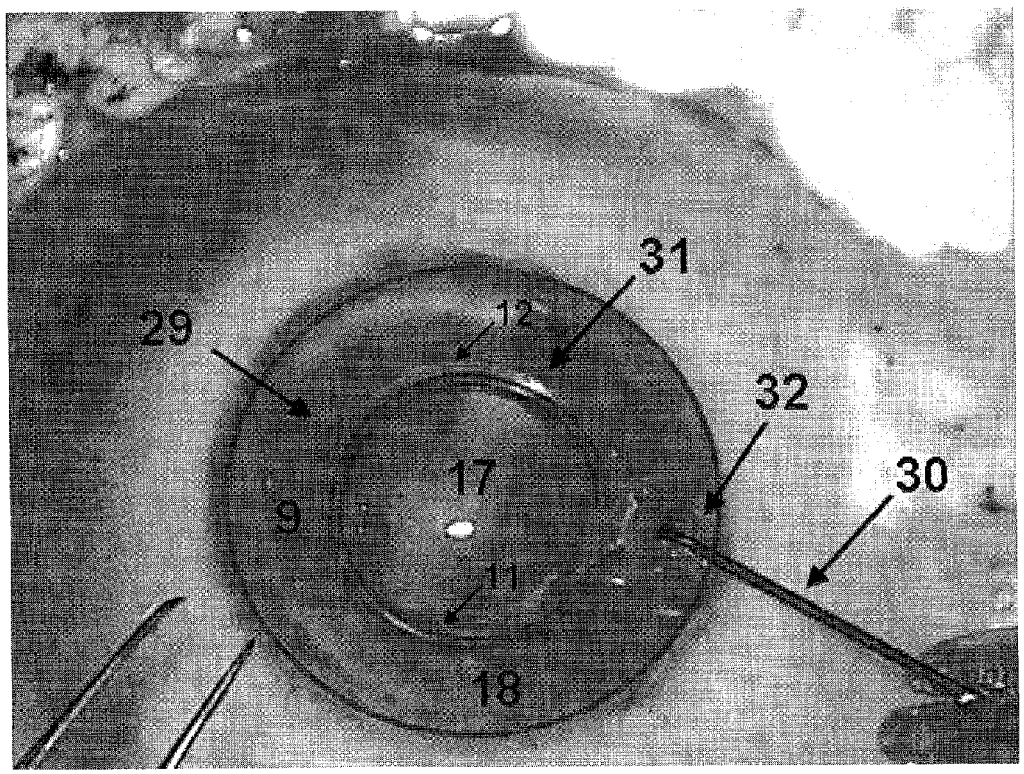
FIG. 8 shows the device resting on a capsule 9. The ring has an inner 11 and outer 12 surfaces. The diameter from inner surface across to the inner surface on the other side is less than the diameter of the capsule. The ring defines an area 17 that is less than the total surface area 18 of the capsule surface shown within the larger circle.
Figure 9:
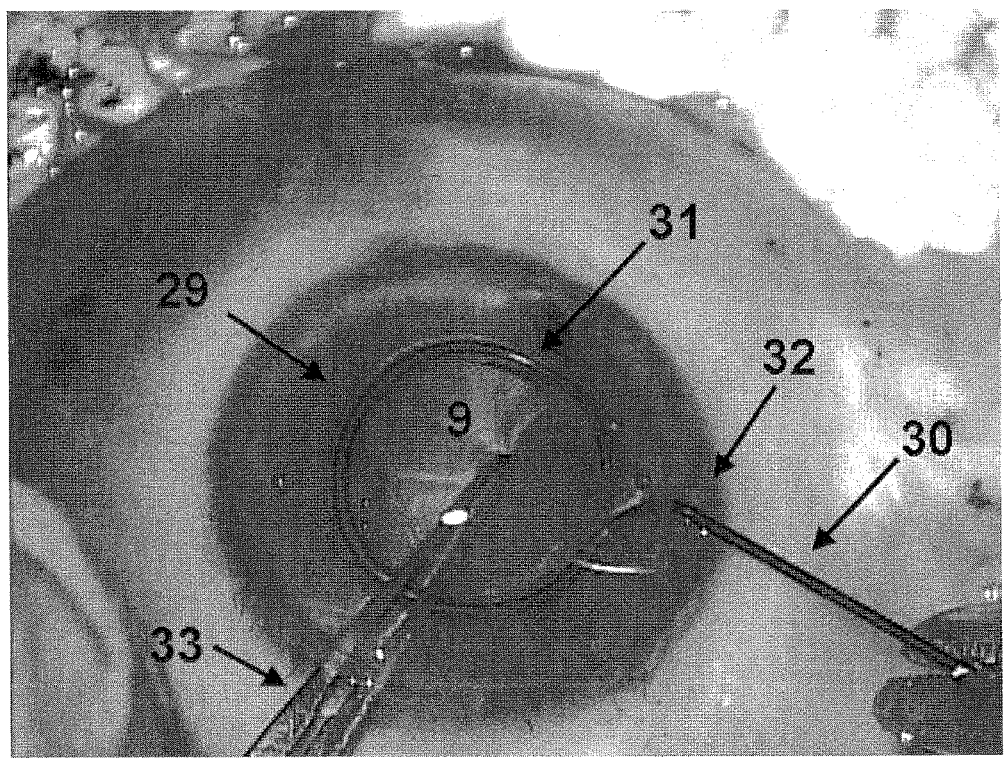
FIG. 9 shows making the initial tear of the capsulorhexis. Here forceps 33 are inserted through an incision 32. The forceps 33 grip the anterior capsule of the eye 9. The device 21 aids in creating the margin.
Figure 10:
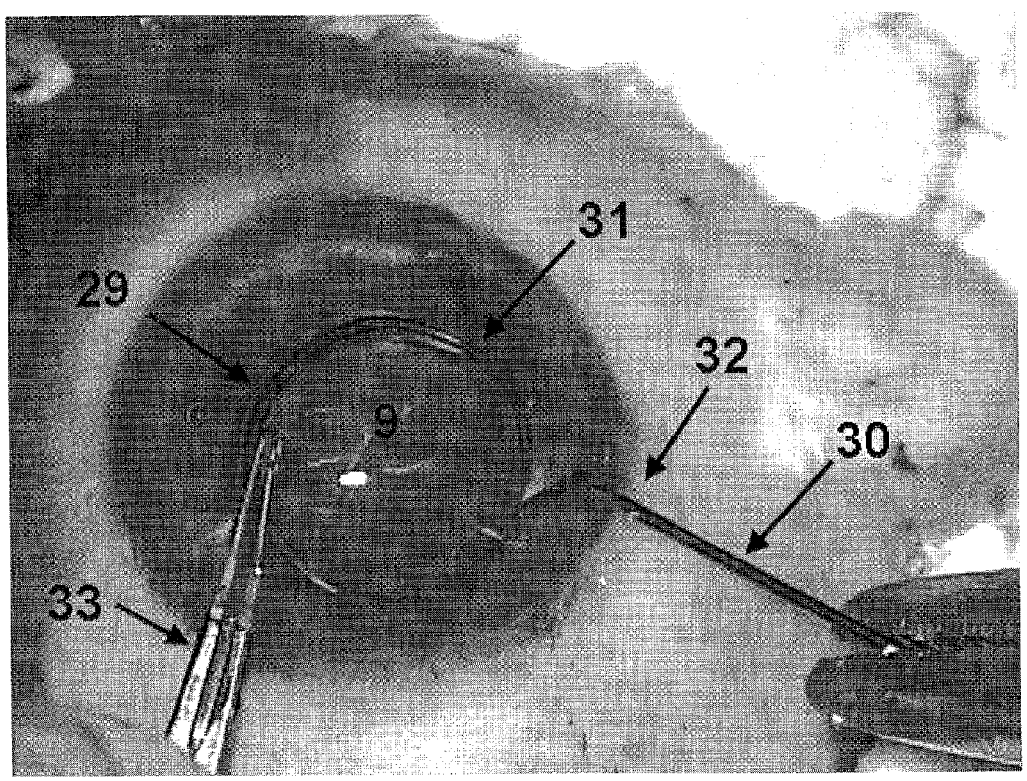
FIG. 10 shows performance of capsulorhexis. Here forceps 33 are inserted through an incision 32. The forceps 33 continue to work with the device 21 in creating the margin the anterior capsule of the eye 9.
Figure 11:
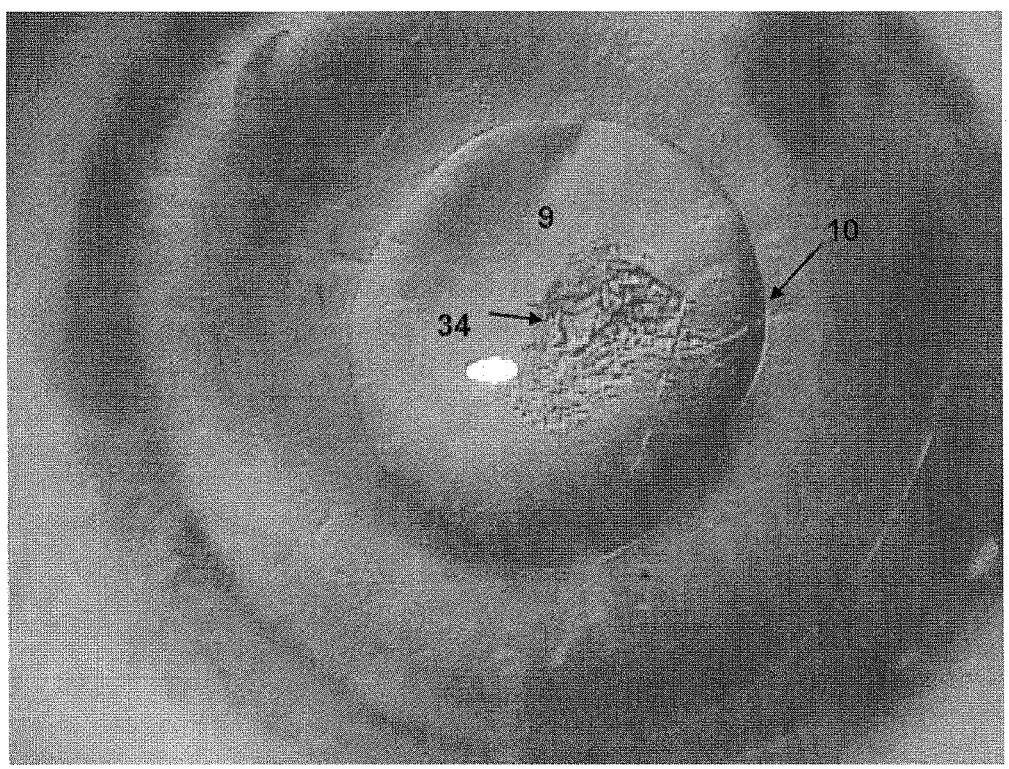
FIG. 11 shows the completed capsulorhexis with device removed. The path of capsulorhexis tissue removal 10 is shown with the excised tissue 34 in the center, before removal from the eye.

The shortfalls of the previous designs can be summarized as follows: first, there was less than optimum adhesion between the device and the capsule to prevent radial tears, and in the case of the first device, an insufficiently sharp edge to cut the capsule without tangential tears. To address these issues, the $4^{th}$ design embodiment combined the greater contact area of a flexible polymeric ring with the downward forces of a nitinol ring. Several silicone rings with an outer diameter of approximately 6.5 millimeters and an inner diameter of 5.5 millimeters were constructed using punch biopsies and fine scissors. The concept called for the silicone rings to be inserted into the anterior chamber, followed by injecting viscoelastic to keep the rings in place over the capsule, and finally placing a nitinol guide wire (from Embodiment 2) over the silicone ring. The nitinol wire would be used to gently press the silicone ring against the capsule, and a manual capsulorhexis would be performed within the silicone ring donut hole using an Utrata forceps, see FIG. 7.

In benchside testing, this approach successfully allowed guidance of a manual capsulorhexis in bovine eyes. Three human eyes were also tested with successful creation of a CCC using an Utrata forceps without radial tears. Each capsulorhexis was appropriately centered and circular, see FIG. 8, FIG. 9, FIG. 10, and FIG. 11. Each of the 3 CCC's measured 5.5 millimeters in diameter as intended. During the testing of this embodiment, it was noted that the nitinol guidewire was still relatively cumbersome to use and required expansion of the corneal incision to 3.5 millimeters to allow for insertion. It was decided that a self-adhering silicone ring would satisfy all of the properties desired for this device.

Embodiment 5: Micropatterned Silicone Ring

Given the success of the $4^{th}$ embodiment, a focus was put upon testing a free standing silicone ring with a micropatterned surface designed to enhance adherence to wet surfaces, as well as help correct a radially directed rhexis if it were to occur. The design was made of silicone with a smooth surfaces superiorly and on the inner and outer wall regions. Positioning holes, horizontal 36 or vertical 38, were put through the ring to enable positioning and are used to facilitate moving the device from side to side or up and down and used to help insert or extract the device. The inferior surface was altered, using an etching laser, to introduce multiple radially offset circumferential features across the entire diameter of the ring. These micropatterns 39 may provide a surface, which better adheres to the surface of the anterior capsule. These features were 50 microns deep, spaced 30 microns apart, see FIG. 13. A closer view of the micropatterning is shown in FIG. 14. The inner diameter of the ring was designed to be flush with the capsule at a sharp right angle with the first etched ring on the inferior surface placed 30 microns away from the inner diameter rim, see FIG. 12.

The device was placed in the anterior chamber of an ex vivo human eye through a 2.4 millimeter incision placed in clear cornea. Additional cohesive viscoelastic was then placed over the ring which was centered over and gently pressed against the anterior capsule using the cannula attached to the viscoelastic. The ring was found to be adherent to the anterior capsule and resisted tangential pressure designed to displace it from side to side. It was however easily displaced off the capsule by an upward motion against the inner or outer rim of the ring using an Utrata forceps. To initiate the CCC, the Utrata forceps was inserted through the 2.4 millimeters incision and a manual rhexis was created using the inner part of the ring to guide the leading edge of a CCC. In each case, the CCC was 5.5 millimeters without evidence of tears or discontinuities. This was repeated on 4 ex vivo human eyes without complications, see FIG. 15, FIG. 16, FIG. 17, FIG. 18, and FIG. 19. During the process of creating the CCC, it was considered if the gaps between the circular patterns on the undersurface of the device could redirect a radially directed rhexis.

Figure 12:
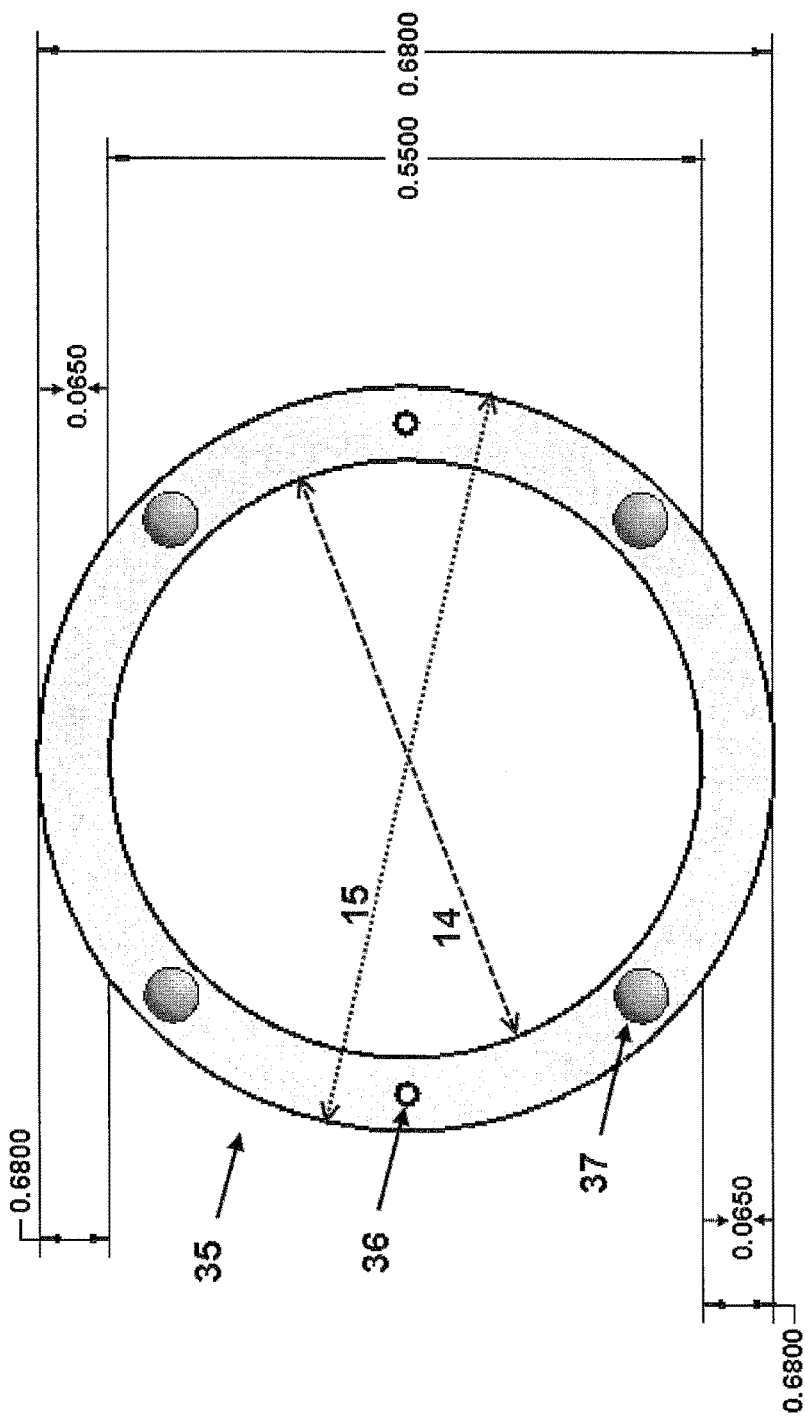
FIG. 12 shows a top side view of the fifth embodiment of the device 35. This view shows horizontal positioning holes 36 that are part of the ring to enable positioning and are used to facilitate moving the device from side to side or up and down and used to help insert or extract the device. The larger circular depression 37 in the top side of the device 35 are used to allow positioning of the device with a tool and for holding the device 35 in place. A positioning tool may sit in the depression 37 to push the device against the capsule if needed.

A view of the top side view of the fifth embodiment of the device 35 is found in FIG. 12. This view shows horizontal positioning holes 36 that are part of the ring to enable positioning and are used to facilitate moving the device from side to side or up and down and used to help insert or extract the device. The larger circular depression 37 in the top side of the device 35 are used to allow positioning of the device with a tool and for holding the device 35 in place. Additionally the ring may contain upper 41 and lower 40 tabs with a gap in between 42 that extend from the outer surface of the ring 15. A positioning tool may sit in the depression 37 to push the device against the capsule if needed. FIG. 12 shows the diameter defined by the outer diameter 15 (0.68) and inner diameter 14 (0.55).

Figure 13:
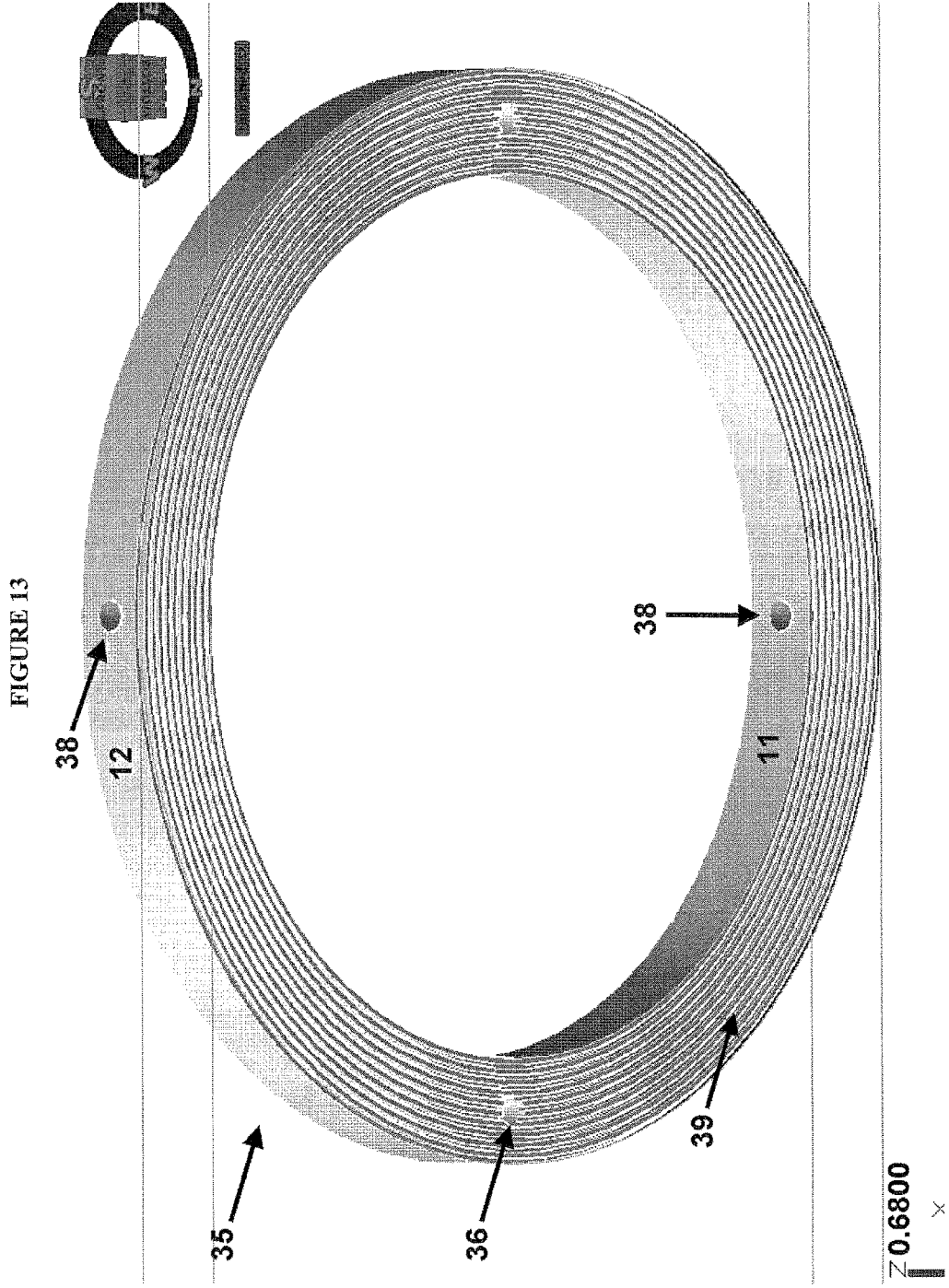
FIG. 13 shows an underside view of the fifth embodiment of the device 35. This view shows concentric ring micropatterning 39 on the posterior surface 13 of the device 35. This view shows positioning holes, horizontal 36 or vertical 38, that are part of the ring to enable positioning and are used to facilitate moving the device from side to side or up and down and used to help insert or extract the device. The inner 11 and outer 12 surfaces are indicated. The ring may be a circle, oval or ellipse.
Figure 14:
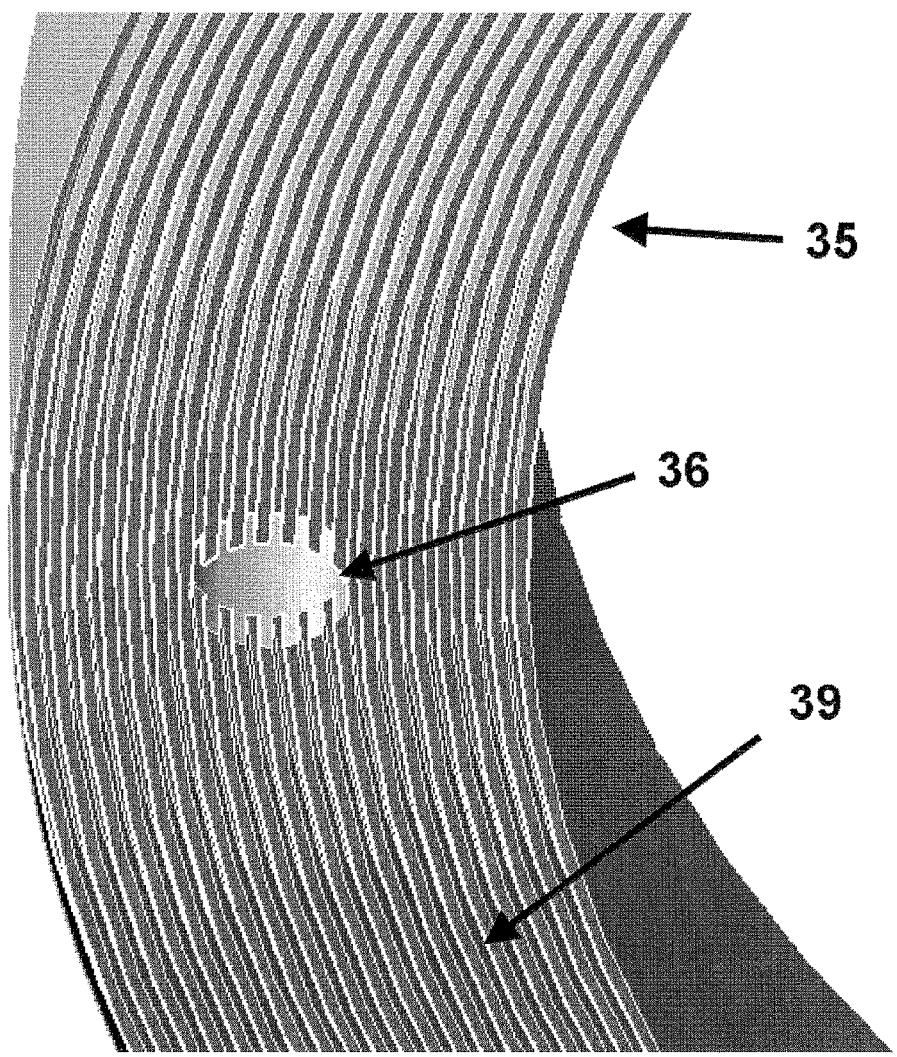
FIG. 14 shows a close up of concentric ring micropatterning 39 on the underside of the fifth embodiment of the device 35.

A view of the underside view of the fifth embodiment of the device 35 is found in FIG. 13. This view shows concentric ring micropatterning 39 on the posterior surface 13 of the device 35. This view shows positioning holes, horizontal 36 or vertical 38, that are part of the ring to enable positioning and are used to facilitate moving the device from side to side or up and down and used to help insert or extract the device. The inner 11 and outer 12 surfaces are indicated. The ring may be a circle, oval or ellipse.

A close up of concentric ring micropatterning 39 on the posterior surface 13 of the fifth embodiment of the device 35 is found in FIG. 14.

Figure 15:
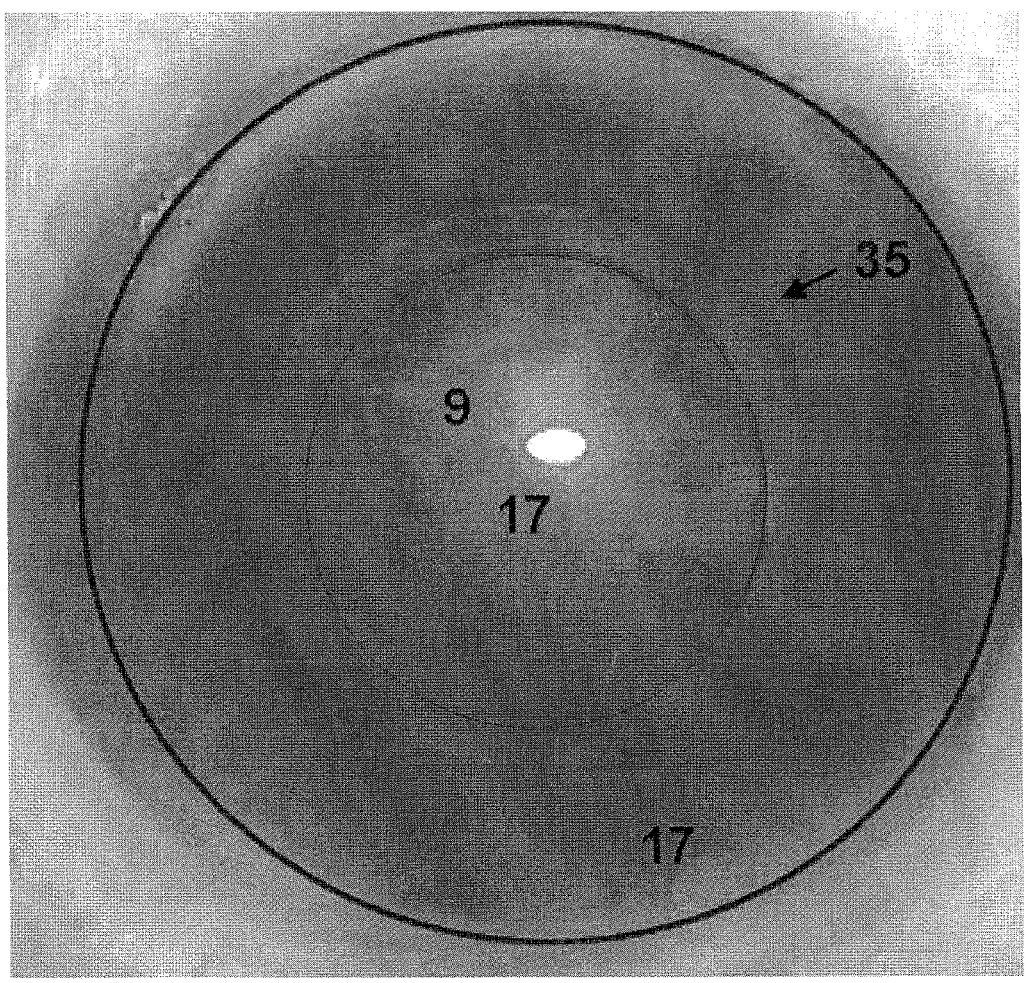
FIG. 15 shows the fifth embodiment of the device 35 sitting on the anterior capsule prior to start of rhexis. This shows the device 35 after positioning of the device 35 upon the anterior capsule of the eye 9. The ring defines an area 17 (whether measured from inner surface to inner surface or measured from outer surface to outer surface) that is smaller than the total surface area 18 of the capsule, indicated by the outer dark ring.

FIG. 15 shows the fifth embodiment of the device 35 sitting on the anterior capsule prior to start of rhexis. This shows the device 35 after positioning of the device 35 upon the anterior capsule of the eye 9. The ring defines an area 17 (whether measured from inner surface to inner surface or measured from outer surface to outer surface) that is smaller than the total surface area 18 of the capsule, indicated by the outer dark ring. The posterior surface 13 of the device has an inner diameter which provides the border from which the capsulorhexis may take place.

Figure 16:
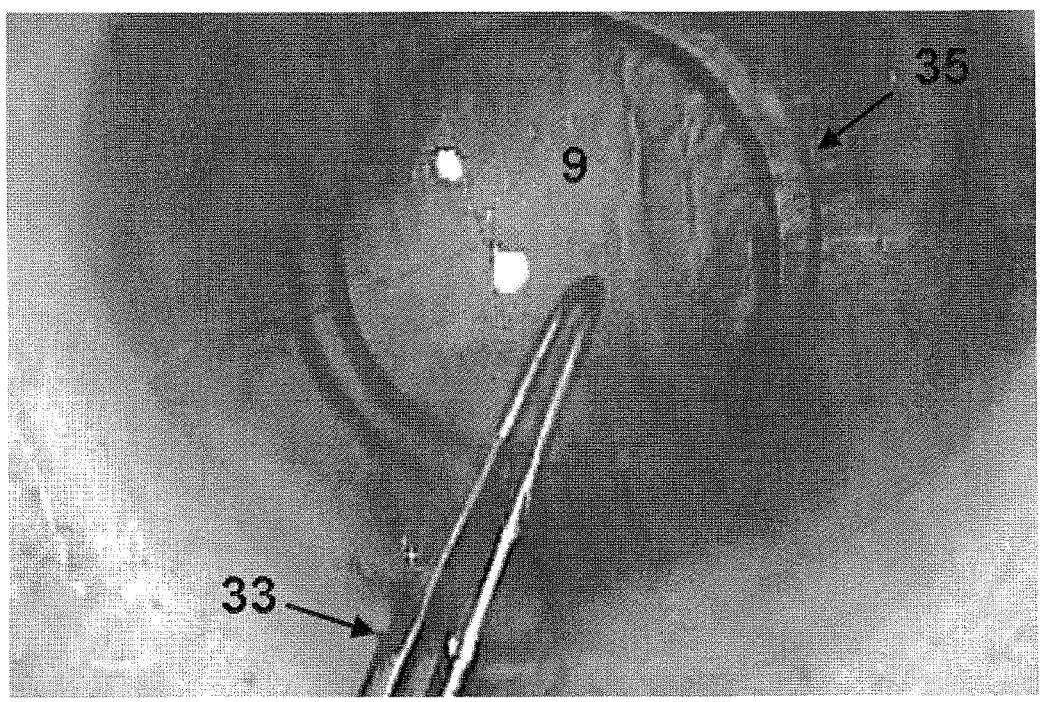
FIG. 16 shows utrata forceps walking rhexis along inner ring of the fifth embodiment of the device 35. This shows the part of the method comprising pulling said ocular anterior lens capsule tissue 9 against said inner ring diameter of the device 35 wherein said capsule is cut.

FIG. 16 shows utrata forceps walking rhexis along inner ring of the fifth embodiment of the device 35. This shows the part of the method comprising pulling said ocular anterior lens capsule tissue 9 against said inner diameter of the posterior surface 13 of the device 35 wherein said capsule is cut.

Figure 17:
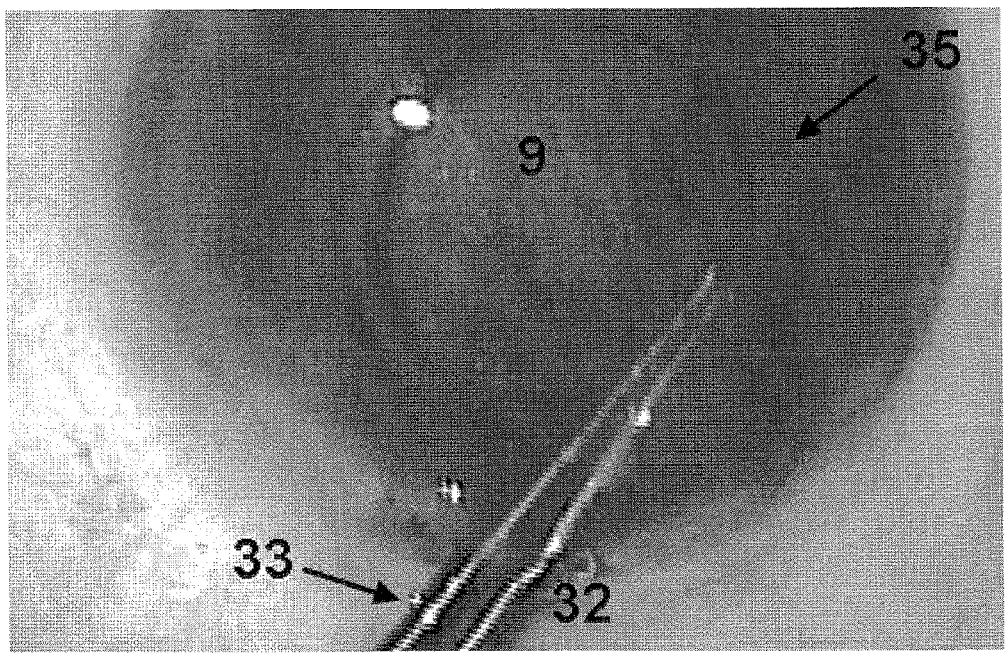
FIG. 17 shows utrata forceps completing rhexis using the fifth embodiment of the device 35. Here the path of capsulorhexis tissue removal 10 is completed in the circle that is defined by the inner diameter of the device 35. The forceps 33 pull upon the ocular anterior lens capsule tissue 9 within the inner diameter of the device 35 through the incision 32 and the excised tissue 34 is almost completely detached.

FIG. 17 shows utrata forceps completing rhexis using the fifth embodiment of the device 35. Here the path of capsulorhexis tissue removal 10 is completed in the circle that is defined by the inner diameter of the posterior surface 13 of the device 35. The forceps 33 pull upon the ocular anterior lens capsule tissue 9 within the inner diameter of the posterior surface 13 of the device 35 through the incision 32 and the excised tissue 34 is almost completely detached.

Figure 18:
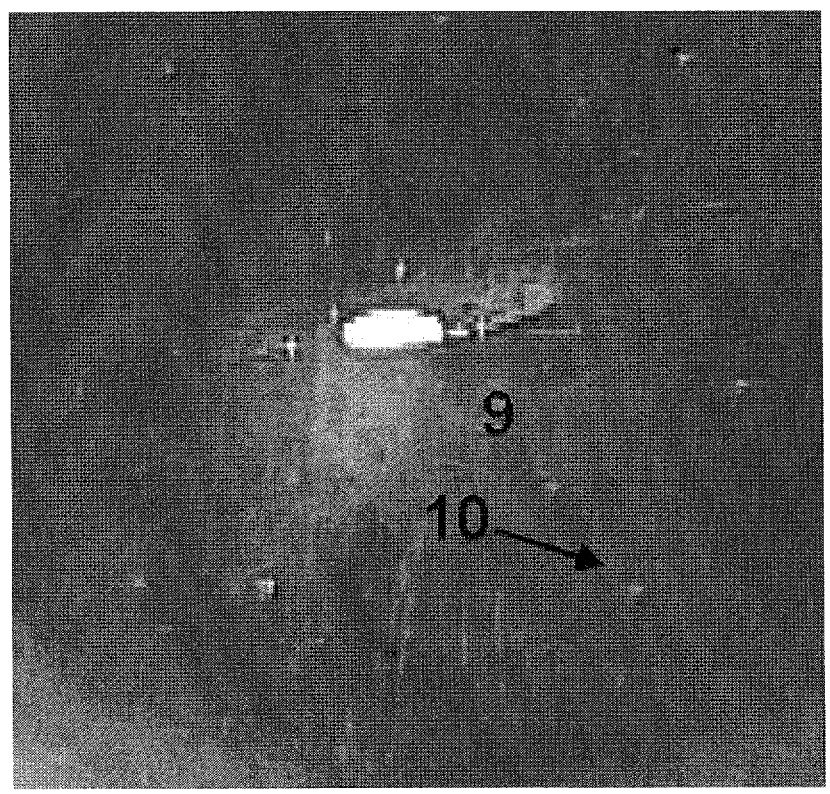
FIG. 18 shows the end result of a continuous curvilinear capsulorhexis using the fifth embodiment of the device 35 of 5.5 millimeters without evidence of tears or discontinuities. This was repeated on 4 ex vivo human eyes without complications. Here the path of capsulorhexis tissue removal 10 is visible and the device 35 has been removed through the incision 32. The excised tissue 34 has also been removed.

FIG. 18 shows the end result of a continuous curvilinear capsulorhexis using the fifth embodiment of the device 35 of 5.5 millimeters without evidence of tears or discontinuities. This was repeated on 4 ex vivo human eyes without complications. Here the path of capsulorhexis tissue removal 10 is visible and the device 35 has been removed through the incision 32. The excised tissue 34 has also been removed.

FIG. 19 shows one embodiment of the device wherein the ring may contain upper 41 and lower 40 tabs with a gap in between 42 that extend from the outer surface of the ring for some distance and contain any encroaching tissues, such as iris, away from the ring surface. The upper and lower tabs can be found spaced at variable distances around the outer ring surface. The tabs may be offset slightly to receive iris tissue without displacing the posterior surface 13 of the device from a given plane.

In subsequent testing, a manual rhexis was initiated in 2 ex vivo human eyes and the rhexis was intentionally directed radially for 1 clock hour. The micropatterned silicone ring was then introduced into the anterior chamber and placed over the radially directed rhexis so that the etched pattern was directly over the leading edge of the rhexis. The capsule was then re-grasped with the Utrata and displaced centrally to attempt redirection of the rhexis back into a non-radial direction, similar to the "little technique" [1]. In each case, the circular micropatterns redirected the rhexis to the inner rim of the silicone ring allowing for continuation of the rhexis without radial tears. The patterned rings appear to act a "stop gap" and help redirect any errantly directed capsular tear.

Discussion

An appropriately executed capsulorhexis is important for successful outcomes in cataract surgery. Suitable continuity in the tear ensures capsular strength [2], predicable size ensures the safety of hydrodissection [3], which aids in effective cortical cleanup and prevention of posterior capsule opacification [4]. Prevention of radial tears is important for proper fixation and centration of posterior chamber IOL's, as well as prevention of a dropped nucleus [5-7]. A suitably small rhexis of 5.5 millimeters, which allows for overlap of the capsule and implanted optic prevents posterior capsule wrinkling and opacification [8]. Proper positioning and power calculation of multifocal and accommodating IOL's also depends on reliable overlap between the capsule and the optic [9], and most accommodating IOL's should not be implanted when radial tears are present [10]. Finally, anterior capsulotomy must also be adequately large, as inappropriately small capsulotomies may lead to phimosis and hyperopic shift [11].

CCC is one of the most difficult techniques for the novice cataract surgeon to master [12], and is made even more difficult in certain situations as previously noted [13]. For these reasons, a reliable guiding and assistive device would be extremely advantageous to surgeons of all experience levels. In addition, the ability to prevent and rescue a radial tear increases the chances for postoperative success. Though many rescue techniques have been described, none provide a consistently reliable ability to redirect the tear [1, 14-19]. Thus, a guiding device that not only prevents, but also corrects radial tears would be a valuable addition to any refractive surgeon's toolkit.

Several techniques and devices exist that ostensibly eliminate the need for a traditional tearing capsulorhexis while still allowing for more precise control of anterior capsulotomy. These include including the Nd:YAG laser, fugo blade, and radiofrequency diathermy [20-23]. While these techniques can potentially mitigate the risk of radial tears, Nd:YAG laser capsulotomy carries a risk of corneal endothelial damage [24], the fugo blade may create capsular margin irregularities [25], and radiofrequency diathermy creates a weaker capsular edge than traditional CCC [26]. In addition, these technologies require expensive equipment not available in many resource-limited settings.

Recently, femtosecond (FS) laser capsulotomy has been introduced as a novel technique that holds the promise for quicker, stronger, more precise anterior capsulotomies [13], which also require less subsequent phacoemulsification power [27]. Such predictably precise geometry and strength are indeed important for myriad reasons, including those mentioned above. Despite the promises of this technology, there are important limitations to its use. First, the technique is relatively contraindicated in cases of corectopia, poor pupillary dilation, and posterior synechiae due to the need in these circumstances for relatively greater dilation [28]. The device is also relatively contraindicated in the setting of glaucoma due to elevation in intraocular pressure at time of docking system suction. The FS laser technique has been associated with cases of posterior capsule rupture and lens dislocation following hydrodissection, otherwise known as capsular block syndrome [29]. Additionally, there are no long-term data to demonstrate that laser capsulotomy actually leads to significantly better visual and refractive outcomes than manual capsulorhexis when executed by experienced surgeons [30].

Perhaps the most important limitation to FS laser technology is its cost. Initial cost of femtosecond laser assisted cataract surgery (FLACS) systems will likely remain in the $400,000-$500,000 range. Usage fees for individual cases will probably continue to range from $150-$400 per eye. And maintenance costs for such systems will probably reach $40,000-$50,000 per year [31]. At present there are no established reimbursement schedules from public or private entities for FLACS [32, 33], which makes it difficult to justify the purchase of this system in all but very high-volume settings. The cost benefit analysis remains elusive at this time but there is great potential for this technology to mature and become more commonly used for ophthalmic procedures.

Cost becomes even more an issue when considering the scale of the problem in resource-limited settings. Approximately 90% of blindness worldwide is due to cases in developing countries [34], with about 50% of these cases due to cataracts [35]. More than 90% of cataract-related disability life-adjusted years occurs in developing countries [36], and cataract surgery is one of the most cost-effective surgeries in this setting [37]. The ability of providers to perform a satisfactory CCC at a reasonable cost is therefore crucial to global eye health.

The fifth device embodiment allows for just this, a highly precise and reproducible capsulorhexis, with the strength and marginal regularity of a traditional continuous tear, at a fraction of the cost of more advanced systems. The present device obviates the need for extensive surgical experience in mastering the CCC technique, opening the door to high-quality cataract surgery even in the hands of less experienced providers such as the training resident. For highly experienced surgeons, the present device would provide additional benefit in special cases such as mature cataract, where capsulorhexis is more difficult. Because it requires no external parts or electricity, it can be used in the most economically bereft settings. Since the present device ensures predictable size and geometry, capsular overlap and IOL centration will be consistent. Centration can also leverage intraoperative data regarding optical axis, angle kappa and aberrometry to enhance CCC centration in real time [38, 39]. This means that postoperative outcomes and optics will be significantly improved, especially in light of the increasing popularity of multifocal and accommodating IOL's that rely on proper centration relative to the pupil.

The fifth embodiment, a silicone ring with micropatterned surface, allows for reproducible execution of a predictably sized capsulorhexis. Because of the low cost of materials involved, ease of use and portability, this device may help improve operative outcomes of cataract surgery in both the developed and developing world.

There may be some limitations to the evaluation described herein that must be considered. First, because the first three embodiments of the design were performed in an open-sky bovine model, it cannot be ruled out that these devices were unfairly challenged by the present approach. Secondly, the fifth embodiment design has not been tested with other materials commonly used for eye implants such as hydrophilic and hydrophobic acrylic polymers. These materials, which are specifically contemplated for devices of the type described herein, would be amenable to micropatterning and current studies are underway to compare how different polymers perform leveraging the present ring design. Addressing these questions in future experiments will strengthen the argument for use of the present device over more expensive technologies, as well as improve the feasibility for its use in a variety of settings.

Thus, specific compositions and configurations of devices and methods for creating a predictable capsulorhexis of specific diameter have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

REFERENCES

1. Little, B. C. et al. (2006) "Little capsulorhexis tear-out rescue," *J. Cataract. Refract. Surg.* 32(9), 1420-1422.
2. Assia, E. I. et al. (1991) "The elastic properties of the lens capsule in capsulorhexis," *Am. J. Ophthalmol.* 111(5), 628-632.
3. Krag, S. et al. (1993) "Strength of the lens capsule during hydroexpression of the nucleus," *J. Cataract. Refract. Surg.* 19(2), 205-208.
4. Apple, D. J. et al. (2000) "Surgical prevention of posterior capsule opacification: Part 1: progress in eliminating this complication of cataract surgery," *J. Cataract. Refract. Surg.* 26(2), 180-187.
5. Wasserman, D. et al. (1991) "Anterior capsular tears and loop fixation of posterior chamber intraocular lenses," *Ophthalmology* 98(4), 425-431.
6. Aasuri, M. K. et al. (2001) "Risk factors for and management of dropped nucleus during phacoemulsification," *J. Cataract. Refract. Surg.* 27(9), 1428-1432.
7. Ram, J. et al. (1999) "Update on fixation of rigid and foldable posterior chamber intraocular lenses. part I: elimination of fixation-induced decentration to achieve precise optical correction and visual rehabilitation," *Ophthalmology* 106(5), 883-890.
8. Hollick, E. J. et al. (1999) "The effect of capsulorhexis size on posterior capsular opacification: one-year results of a randomized prospective trial," *Am. J. Ophthalmol.* 128(3), 271-279.

9. Cekiç, O and Batman, C. (1999) "The relationship between capsulorhexis size and anterior chamber depth relation," *Ophthalmic Surg. Lasers* 30(3), 185-190.
10. Palanker, D. et al. (2010) "Anterior capsulotomy with a pulsed-electron avalanche knife," *J. Cataract. Refract. Surg.* 36(1), 127-132.
11. Sanders, D. R. et al. (2006) "Hyperopic shift in refraction associated with implantation of the single-piece Collamer intraocular lens," *J. Cataract. Refract. Surg.* 32(12), 2110-2112.
12. Dooley, I. J. and O'Brien, P. D. (2006) "Subjective difficulty of each stage of phacoemulsification cataract surgery performed by basic surgical trainees," *J. Cataract. Refract. Surg.* 32(4), 604-608.
13. Friedman, N. J. et al. (2011) "Femtosecond laser capsulotomy," *J. Cataract. Refract. Surg.* 37(7), 1189-1198.
14. Mohammadpour, M. (2010) "Rescue of an extending capsulorrhexis by creating a midway tangential anterior capsular flap: a novel technique in 22 eyes," *Canadian Journal of Ophthalmology/Journal Canadien d'Ophtalmologie* 45(3), 256-258.
15. Coelho, R. P. et al. (2012) "Capsulorhexis rescue after peripheral radial tear-out: Quick-pull technique," *J. Cataract. Refract. Surg.* 38(5), 737-738.
16. Das, P. et al. (2009) "Results of intraocular lens implantation with capsular tension ring in subluxated crystalline or cataractous lenses in children," *Indian J. Ophthalmol.* 57(6), 431-436.
17. Carifi, G. and Zuberbuhler, B. (2012) "Capsulorrhexis rescue techniques," *J. Cataract. Refract. Surg.* 38(10), 1874-1875.
18. Karim, S. M. R. et al. (2011) "A novel technique of rescuing capsulorhexis radial tear-out using a cystotome," *Journal of Visualized Experiments* (47), 2317.
19. Wu, M. C. and Bhandari, A. (2008) "Managing the broken capsule," *Curr Opin. Ophthalmol.* 19(1), 36-40.
20. Singh, D. (2002) "Use of the Fugo blade in complicated cases," *J. Cataract. Refract. Surg.* 28(4), 573-574.
21. Coelho, R. P. et al. (2009) "Comparison of preoperative Nd:YAG laser anterior capsulotomy versus two-stage curvilinear capsulorhexis in phacoemulsification of white intumescent cataracts," *Ophthalmic Surgery, Lasers & Imaging* 40(6), 582-585.
22. Fugo, R. J. (2006) "Fugo blade to enlarge phimotic capsulorhexis," *J. Cataract. Refract. Surg.* 32(11), 1900.
23. Gassmann, F. et al. (1988) "Anterior capsulotomy by means of bipolar radio-frequency endodiathermy," *J. Cataract. Refract. Surg.* 14(6), 673-676.
24. Vaikoussis, E. et al. (1993) "Corneal endothelial damage after Nd:YAG laser anterior capsulotomy," *Doc. Ophthalmol.* 83(4), 279-286.
25. Izak, A. M. et al. (2004) "Analysis of the capsule edge after Fugo plasma blade capsulotomy, continuous curvilinear capsulorhexis, and can-opener capsulotomy," *J. Cataract. Refract. Surg.* 30(12), 2606-2611.
26. Morgan, J. E. et al. (1996) "The mechanical properties of the human lens capsule following capsulorhexis or radiofrequency diathermy capsulotomy," *Arch. Ophthalmol.* 114(9), 1110-1115.
27. Nagy, Z. et al. (2009) "Initial clinical evaluation of an intraocular femtosecond laser in cataract surgery," *J. Refract. Surg.* 25(12), 1053-1060.
28. Nagy, Z. Z. (2012) "Advanced Technology IOLs in Cataract Surgery: Pearls for Successful Femtosecond Cataract Surgery," *Int. Ophthalmol. Clin.* 52(2), 103-114.
29. Roberts, T. V. et al. (2011) "Capsular block syndrome associated with femtosecond laser-assisted cataract surgery," *J. Cataract. Refract. Surg.* 37(11), 2068-2070.
30. Trikha, S. et al. (2013) "The journey to femtosecond laser-assisted cataract surgery: new beginnings or a false dawn?," *Eye* 27(4), 461-473.
31. Bethke, W. (2011) "Can you afford to do a femtosecond cataract?," *Review of Ophthalmology* 18, 52.
32. Cimberle, M. (2012) "Femtosecond laser assisted surgery could revolutionize cataract removal in Europe," *Ocular Surgery News* 23, 1.
33. American Academy of Ophthalmology. (2012) "Eye-Surgery Organizations Provide Medicare-Billing Guidance to Physicians for Laser Technology Used in Cataract Procedures" *American Academy of Ophthalmology News Release.*
34. Cunningham, E. T. (2001) "World blindness—no end in sight," *Br. J. Ophthalmol.* 85(3), 253-254.
35. Lawani, R. et al. (2007) "[Magnitude and strategies of cataract management in the world]," *Med. Trop. (Mars.)* 67(6), 644-650.
36. Ono, K. et al. (2010) "Global inequality in eye health: country-level analysis from the Global Burden of Disease Study," *Am. J. Public Health* 100(9), 1784-1788.
37. Baltussen, R. et al. (2004) "Cost-effectiveness analysis of cataract surgery: a global and regional analysis," *Bull. W.H.O* 82(5), 338-345.
38. Park, C. Y. et al. (2012) "Measurement of angle kappa and centration in refractive surgery," *Curr. Opin. Ophthalmol.* 23(4), 269-275.
39. Soda, M. and Yaguchi, S. (2012) "Effect of Decentration on the Optical Performance in Multifocal Intraocular Lenses," *Ophthalmologica* 227(4), 197-204.

We claim:
1. A capsulorhexis device comprising:
i) a ring having an outer surface and an inner surface;
ii) a posterior surface connecting said outer surface and said inner surface, wherein said posterior surface comprises a tacky polymer with hydrophobic properties, said posterior surface comprises a micropattern, and said posterior surface is defined by an inner and outer diameter; and
iii) a distinct internal edge positioned on said posterior surface of said inner surface, wherein the micropattern comprises concentric micro-grooves, the capsulorhexis device requiring no electricity.
2. The capsulorhexis device of claim 1, wherein the posterior surface is defined by said inner diameter of at least 4.3 millimeters and said outer diameter is greater than 7.8 millimeters.
3. The capsulorhexis device of claim 1, wherein the posterior surface defined by said inner diameter is between 6.0 millimeters-4.75 millimeters.
4. The capsulorhexis device of claim 1, wherein said capsulorhexis device further comprises upper and lower tabs with a space between them, said upper and lower tabs extending from said outer ring surface.
5. The capsulorhexis device of claim 1, wherein said inner surface has an inner diameter and said outer surface has an outer diameter.
6. The capsulorhexis device of claim 5, wherein said ring has an outer diameter between 6.3-6.0 millimeters and an inner diameter between 5.3-5.0 millimeters.
7. The capsulorhexis device of claim 1, wherein a height of the capsulorhexis device is less than a shortest distance between the inner ring surface and the outer ring surface.

8. The capsulorhexis device of claim 1, wherein said internal edge of said ring is right angled in relation to the posterior surface of said ring.

9. The capsulorhexis device of claim 1, wherein said ring is flexible.

10. The capsulorhexis device of claim 1, wherein said ring is made from a polymer.

11. The capsulorhexis device of claim 10, wherein said polymer is selected from the group consisting of:
medical grade silicone, hydrophobic acrylic, hydrophilic acrylic, and other common medical grade polymers.

12. The capsulorhexis device of claim 10, wherein said ring further comprises a stiffened polymer backbone with a flexible coating.

13. The capsulorhexis device of claim 10, wherein said ring is coupled with a rigid material configured to fix said polymer in place.

14. The capsulorhexis device of claim 13, wherein said rigid material is selected from the group consisting of polypropylene and nitinol.

15. The capsulorhexis device of claim 10, wherein the polymer is hydrophobic.

16. The capsulorhexis device of claim 1, wherein said ring is compressible and after said compression the ring returns to a ring shape.

17. The capsulorhexis device of claim 1, wherein the ring further comprises ports through which suction is applied.

18. A method comprising:
a) providing the capsulorhexis device of claim 1;
b) making an incision in an eye,
c) inserting said capsulorhexis device through said incision, and
d) positioning said capsulorhexis device over an ocular anterior lens capsule, wherein said positioning defines an area for execution of a capsulorhexis with said device.

19. The method of claim 18, wherein said area of execution of capsulorhexis is defined by the inner diameter of said ring.

20. The method of claim 18, wherein said method further comprises pulling said ocular anterior lens capsule against said inner ring diameter whereupon said ocular anterior lens capsule is cut.

* * * * *